(12) United States Patent
Donello et al.

(10) Patent No.: US 7,884,115 B2
(45) Date of Patent: Feb. 8, 2011

(54) METHODS AND COMPOSITIONS FOR THE TREATMENT OF PAIN AND OTHER NEUROLOGICAL CONDITIONS

(75) Inventors: John E. Donello, Dana Point, CA (US); Fabien J. Schweighoffer, Val-de-marne (FR)

(73) Assignee: Allergan, Inc., Irvine, CA (US)

( * ) Notice: Subject to any disclaimer, the term of this patent is extended or adjusted under 35 U.S.C. 154(b) by 847 days.

(21) Appl. No.: 11/575,947

(22) PCT Filed: Sep. 27, 2005

(86) PCT No.: PCT/US2005/034898
§ 371 (c)(1),
(2), (4) Date: Mar. 23, 2007

(87) PCT Pub. No.: WO2006/037069
PCT Pub. Date: Apr. 6, 2006

(65) Prior Publication Data
US 2008/0085920 A1    Apr. 10, 2008

Related U.S. Application Data

(60) Provisional application No. 60/614,356, filed on Sep. 28, 2004.

(51) Int. Cl.
*A61K 31/445* (2006.01)
(52) U.S. Cl. ...................................... 514/315
(58) Field of Classification Search ................... 514/315
See application file for complete search history.

(56) References Cited

U.S. PATENT DOCUMENTS 4,260,622 A    4/1981  Junge et al.
2002/0142985 A1 * 10/2002  Dwek et al. ................... 514/44

OTHER PUBLICATIONS

Victor, M. & Ropper, Alan H., *Principles of Neurology* Ch. 8 153 (7th Ed. 1997).
Kingery, W.S. et al., *Molecular Mechanisms for the Analgesic Properties of Alpha-2 Adrenergic Agonists* in *Molecular Neurobiology of Pain* 275 (IASP Press 1997).
Remington's Pharmaceutical Sciences, Mack Publishing Company, Easton, Pa., (16th Edition, 1980).
van den Spoel, Aarnoud C. et al., *Proc. Natl. Acad. Sci. 99*(Dec. 23, 2002):17173-17178.
Tsuruoka et al., "Synthesis of D-glucero-δ-lactam, an oxidation product of Nojirimycin", SCI. Reports Moeiji Seika Kaisha 13(1973):80-84.
Asano et al, "N-Containing sugars from Morus alba and their glycosidase inhibitory activities", Carbohydr. Res. 1994 Jun. 17;259(2):243-255.
McDonnell et al., "A General Synthesis of Iminosugars", J. Org. Chem. 69(2004):3565-3568.
Singh, et al., "A general methodology for the asymmetric synthesis of 1-deoxyiminosugars", Tetrahedron Letters 44(2003):2387-2391.
van den Broek et al., "Synthesis of oxygen-substituted N-alkyl 1-deoxynojirimycin derivatives: aza sugar α-glucosidase inhibitors showing antiviral (HIV-1) and immunosuppressive activity", Recl. Trav. Chim. Pays-Bas 113(1994):507-516.
Koh and Choi, J. Neurosci. Methods 20(1987): 83-90.
Butters, et al., "Molecular requirements of imino sugars for the selective control of N-linked glycosylation and glycosphingolipid biosynthesis", Tetrahedron:Asymmetry 11(2000):113-124.
Minami et al, "Allodynia evoked by intrathecal administration of prostaglandin $E_2$ to conscious mice", Pain, 57 (1994): 217-223.
Dixon, "Efficient Analysis of Experimental Observations", Ann. Rev. Pharmacol. Toxicol, 1980, 20: 441-462.

* cited by examiner

*Primary Examiner*—Jennifer M Kim
(74) *Attorney, Agent, or Firm*—Joel B. German; Debra D. Condino; Allergan, Inc.

(57) ABSTRACT

Methods and compositions for the treatment of conditions including stress-associated, chronic pain, and neurodegenerative conditions in a mammal using a composition comprising NB-DNJ or a compound structurally similar thereto.

4 Claims, 9 Drawing Sheets

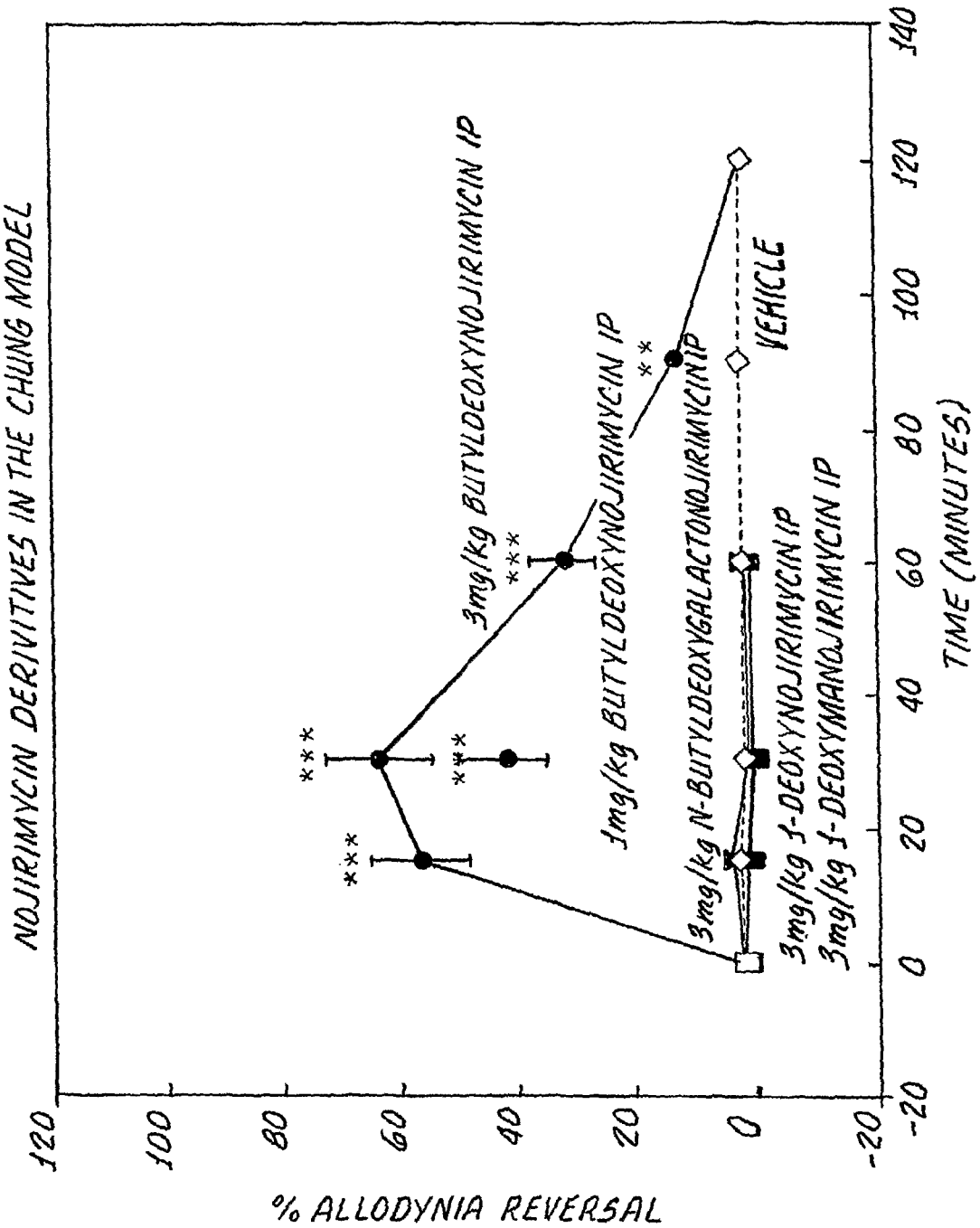

NB-DNJ EFFECT ON KAINITE-INDUCED
TOXICITY IN NEURON CULTURE

NB-DNJ EFFECT ON KAINITE-INDUCED
TOXICITY IN NEURON CULTURE

NB-DNJ EFFECT ON KAINITE-INDUCED
TOXICITY IN NEURON CULTURE

NB-DNJ EFFECT ON NMDA-INDUCED TOXICITY

NB-DNJ EFFECT ON NMDA-INDUCED TOXICITY

DNJ EFFECT ON KAINITE-INDUCED TOXICITY

DNJ EFFECT ON KAINITE-INDUCED TOXICITY

DNJ EFFECT ON KAINITE INDUCED TOXICITY

DNJ EFFECT ON NMDA-INDUCED TOXICITY

DNJ EFFECT ON NMDA-INDUCED TOXICITY

METHODS AND COMPOSITIONS FOR THE TREATMENT OF PAIN AND OTHER NEUROLOGICAL CONDITIONS

CROSS REFERENCE TO RELATED APPLICATIONS

This is a national stage application under 35 U.S.C. §371 of PCT application PCT/US2005/034898, filed on Sep. 27, 2005, which claims the benefit of Provisional Application No. 60/614,356 filed on Sep. 28, 2004.

BACKGROUND OF THE INVENTION

Pain is the predominant means by which illness and physical dysfunction are detected in humans and animals. Most diseases involve pain as a symptom, and the absence of pain often signifies the lack of a pathology.

Pain is increasingly seen as having a physical component and a psychological component. Thus, pain may involve a physical sensation, caused by certain stimuli of certain nerves and the subsequent transmission of pain impulses to the central nervous system. Alternatively, or concurrently, pain may involve a stressful state of mind linked to emotion, depression, or anguish. Thus, recently some have begun to regard pain, particularly certain types of pain such as chronic pain (including phantom, allodynia and/or neuropathic pain), as having certain elements in common with psychiatric or neurophysiological and neurodegenerative disorders.

According to current pain theory, the physical sensation of pain is mediated by two types of afferent nerve fibers in the distal axons of primary sensory neurons. These fibers respond maximally to nociceptive (i.e. potentially tissue-damaging) stimuli. One fiber is a very fine, unmyelinated, slowly conducting fiber (the C fiber), and the other is a thinly myelinated, more rapidly conducting fiber termed the A-delta (A-δ) fiber. The peripheral terminals of these primary pain afferents are highly branched nerve endings in the skin and other organs. There are three broad categories (with possible subcategories) of free nerve endings: mechanoreceptors (those that respond to innocuous mechanical stimulation); thermoreceptors (those that respond to innocuous heat stimulation); and polymodal nociceptors (these respond best to noxious stimuli, but can transmit impulses in response to thermal, chemical or mechanical stimuli. Additionally, certain A-delta fibers can respond to light touch, temperature and pressure as well as to pain, and seem to do so in proportion to the level of stimulus.

The peripheral afferent pain fibers have their cell bodies in the dorsal root ganglia. Central extensions of these neurons project to the dorsal horn of the spinal cord, where they terminate. Fast-conducting secondary ascending afferent neurons transmit the pain impulses to nuclei in the thalamus, medulla, pons and midbrain.

Additionally, groups of slowly conducting fibers project, for example, to the reticular core of the medulla and midbrain and then to the medial and intralaminar nuclei of the thalamus. One such group of fibers is called the spinoreticulothalamic pathway. In the medulla, these fibers synapse in the nucleus gigantocellularis.

These slow-conducting fiber systems appear to conduct diffuse, poorly localized pain from deep and visceral structures in the body, and it has been proposed that they are involved in the unpleasant feelings caused by pain, including the psychic aspects of pain, even when the direct, fast-moving pathways have been interrupted. However, neural projections from the ventral posterolateral thalamus project directly to the sensory cortex to mediate the sensory-discriminative aspects of pain, such as location, quality, and perhaps intensity. The pathways for visceral pain from the esophagus, stomach and bowels are carried largely by the vagus nerve and terminate in the nucleus of the solitary tract (NST) before projecting to the thalamus; other abdominal viscera appear to reach the NTS by other pathways, as they still activate the NTS when the vagus nerve is severed.

In addition to the ascending pain pathways from the sensory neurons to the brain, there are also descending pain-related pathways. One such pathway originates in the brain (the frontal cortex and hypothalamus) and projects to the midbrain, pons, medulla and spinal cord. Other descending pathways (e.g., noradrenergic and serotoninergic) originate in the locus coeruleus, dorsal raphe nucleus and nucleus reticularis gigantocellularis and appear to modulate the nociceptive response.

As indicated above, acute nociceptive pain is a reaction to tissue-injuring stimuli, such as pricking, cutting, crushing, burning and freezing. However, these stimuli do not result in pain in all tissues; pain receptors are activated by different stimuli, depending on the tissue. So, for example, in the stomach and intestine pain is produced by stimuli such as inflamed mucosa and distension or spasm of the smooth muscle. In skeletal muscle pain is caused by eschemias, necrosis, hemorrhage, injection of irritating solutions, and prolonged contraction. Distension of arteries (as occurs in thrombolyic and embolic occlusion) can cause pain, as can excessive arterial pulsation. The latter may be a cause (or as has been more recently suggested, a symptom) of migraine pain. Other mechanisms of headache may be neurogenic in nature.

When tissue is damaged there is liberation of proteases from injured cells. These proteases act locally on tissue proteins to directly or indirectly liberate substances that stimulate pain receptors. Some of these substances include histamine, prostaglandins, serotonin and potassium ions. Also, the receptors themselves cause the liberation of pain-enhancing substances such as Substance P, which is released from the nerve endings of C fibers in the skin during peripheral nerve stimulation. Substance P causes erythema and edema and recruits leukocytes in a reaction called neurogenic inflammation.

The threshold of pain perception for a given stimulus is approximately the same for all humans. This pain threshold is reduced by inflammation and in a condition termed allodynia, tissue becomes sensitized such that ordinarily innocuous stimuli, such as light touching or brushing, becomes painful. The pain threshold is increased through administration of anesthetics or analgesics.

The human body comprises a neuronal analgesia system, which can be activated by substances including opiates and naturally occurring brain chemicals, such as the endorphins, having pharmacologic properties of opiates. Stimulation of various loci within the brain results in the suppression of nociceptive responses and are relayed to the dorsal horn gray matter via a pathway in the spinal cord.

Opiates act pre- and post-synaptically in neurons of the A-delta and C fibers, suppressing afferent pain impulses. The endorphins appear to act through an endogenous system stimulated most strongly by prolonged pain and fear; for example, some soldiers wounded in battle appear to require little or no analgesic medication, probably due to activation of this latter system. This phenomenon is known as stress-induced analgesia. As an example of one way in which this system operates, the endorphin enkephalin binds the opiate receptors at the point of entry of pain fibers into the spinal cord and inhibits the release of the chemical transmitter Substance P. Thus, the post-synaptic neuron receives less stimulation by Substance P, and therefore transmits less excitatory pain impulses to the brain.

Descending pain-control systems other than the opiate system have been identified; noradrenergic and serotoninergic pain pathways have been described in mammals, although their precise mechanism has not yet been described. Activation of a norepinephrinergic pathway from the pons to the spinal cord blocks spinal nociceptive receptors, while descending serotoninergic fibers from the medulla inhibit dorsal horn cells concerned with pain transmission.

"Hyperalgesia" is a term that refers to an increased sensitivity to painful stimulus, while "hypoalgesia" connotates the opposite. An increased reaction to a painful stimulus once it is perceived is termed "hyperpathia", which results in the symptom of allodynia. Allodynic pain has unusual features which are modifiable by fatigue, emotion, etc., and is a common feature of neuropathic or neurogenic pain such as pain resulting from peripheral neuropathy. For example, "causalgia" is a specific type of burning pain resulting from interruption of a peripheral nerve.

"Deep pain" from visceral and skeletomuscular structures tends to be aching in quality, and sharp when intense. It is diffuse and poorly localized. "Referred pain" is pain, such as deep pain, which is projected to (felt to occur in) some fixed site at some distance from the source.

In recent years there has begun to be recognition that there is a difference between acute pain (usually associated with the nociceptive receptors and involving potential or actual tissue damage) and the phenomenon of chronic pain. By "chronic pain" is meant to include, without limitation, neuropathic pain, referred pain, phantom pain, allodynia, visceral pain, deep pain, and the like resulting from myriad conditions including, without limitation, arthritis, headache (including tension and migraine headache), musculoskeletal pain (such as back pain) cancer, and bowel disorders, such as irritable bowel syndrome (IBS).

One difference between chronic and acute pain mentioned above concerns the stress-related and psychic effects of chronic pain. Continuous pain increases irritability, fatigue, depression, disturbs sleep, impairs appetite, and can deprive the subject of psychic and physical strength.

Common classes of drugs used as analgesics broadly include opioids, nonopioid analgesics (such as non-steroid anti-inflammatory agents, or NSAIDs), anticonvulsants and tricyclic antidepressants. The effectiveness of each of these drug types for different types of pain indicates that pain is a complex phenomenon in which different mechanisms may be in play depending on the particular nature of the pain stimulus.

NSAIDs such as aspirin, ibuprofen and acetaminophen appear to function by inhibiting the synthesis of prostaglandins and therefore the prostaglandin-mediated activation of nociceptors. Opioids act as "false" neurotransmitters at the endorphin receptor sites in the posterior horns of the spinal cord. Opioids also exert a powerful action of the psychic "affective" component of pain.

Tricyclic antidepressants such as, doxepin, amitriptyline, Imipramine, nortriptyline and Desipramine are used as serotonin reuptake inhibitors (SRIs), thus enhancing the activity of serotonin at synapses and theoretically facilitating the endogenous opiate analgesic system. Some of the newer SRIs do not appear to be as effective as the older, less specific ones, at treating chronic neuropathic pain. Victor, M. & Ropper, Alan H., *Principles of Neurology* Ch. 8 153 (7$^{th}$ Ed. 1997).

Anticonvulsants, such as phenytoin, carbamazepine, clonazepam, and gabapentin, are useful in the treatment of some central and peripheral neuropathic pains, but seem to be less effective at treating causalgic pain. The mechanism of analgesic action of these agents is not understood.

In addition, alpha 2 adrenoreceptors have been long been known to be involved in analgesia, and compounds having alpha 2 agonist activity have been used clinically since 1984. See Kingery, W. S. et al., *Molecular Mechanisms for the Analgesic Properties of Alpha*-2 *Adrenergic Agonists in Molecular Neurobiology of Pain* 275 (IASP Press 1997). Such agents, for example, clonidine, tizanidine and dexmedetomidine—which are not subtype-selective alpha 2 agonists—have mainly been used in perioperative analgesia due to significant sedative and cardiovascular effects. Because of these effects, intrathecal administration has been the route of choice. Systemically administered alpha 2 agonists have been shown to have significant analgesic activity, but treatment has been limited by the lower threshold of sedative activity. Very low systemic doses of clonidine and dexmedetomidine cause sedation, bradycardia and hypotension; indeed, the $ED_{50}$ of these drugs for sedation is significantly lower than the $ED_{50}$ for analgesia.

Particularly with respect to neurological and chronic pain, there appear to be certain commonalities between the biochemistry of pain and that of neurological and neurodegenerative disease. For example, nerve injury, such as nerve crush or ligation, is often used as a model for both chronic pain and for neurodegenerative disorders such as glaucoma. Also, some neurological diseases, such as certain forms of Charcot-Marie-Tooth syndrome (a group of conditions affecting the function or structure of peripheral nerve axons or the lipid-containing myelin sheath encasing them) involve disorders of lipid metabolism or catabolism.

Neurodegeneration is a term which includes the apoptotic destruction of neuronal tissue as well as the degenerative disorders involving neuronal, myelin, or tissue breakdown, with degradation products liberated from damaged cells evoking even more tissue destruction and phagocytosis. Conditions involving apoptosis are usually gradual and not metabolically based; those involving the more traumatic degenerative processes often have a metabolic origin.

Many diseases involving neurodegeneration begin gradually after a long period of normal nervous system function and are progressive, usually over a period of years. Among such conditions, without limitation, are:

I. Syndromes of Progressive Dementia (e.g., Alzheimer's disease, diffuse cerebral cortical atrophy of non-Alzheimer's origin, Lewy body dementia, Pick disease, frontotemporal dementia, thalamic dementia, Huntington chorea, non-Huntington chorea, cortical-striatal-spinal degeneration (Jakob) and the dementia-Parkinson-amyotrophic lateral sclerosis complex, dentatorubropallidoluysian degeneration (DRPLA), cerebrocerebellar degeneration, familial dementia with spastic paraparesis, amyotrophy, or myoclonus, Lewy body disease, Parkinson disease (some cases), corticobasal ganglionic degeneration, polyglucosan body disease)

II. Syndrome of Disordered Posture and Movement (e.g., Parkinson's disease, Shy-Drager syndrome, multiple system atrophy, progressive supranuclear palsy, dystonia, Hallervorden-Spatz disease, corticobasal ganglionic degeneration, torticollis, Meige syndrome, familial tremors, Tourette syndrome, acanthocytic chorea)

III. Syndrome of Progressive Ataxia (e.g., Friedreich ataxia, non-Friedreich early onset ataxia, cerebellar cortical ataxias, olivopontocerebellar degenerations (OPCA), dentatorubral degeneration (Ramsey Hunt type), dentatorubropallidoluysian atrophy, Machado-Joseph, Azorean disease, other ataxias with retinopathy, pigmentary retinopathy, ophthalmoplegia, slow eye movements (Wadia), neuropathy, optic atrophy, deafness and dementia.)

IV. Syndrome of Slowly Developing Muscular Weakness or Atrophy (e.g., amyotrophic laterial sclerosis (ALS), progressive spinal muscular atrophy, progressive bulbar palsy, spastic paraplegia, primary lateral sclerosis)

V. Sensory and Sensorimotor Disorders (e.g., Charcot-Marie-Tooth syndrome, hypertrophic interstitial polyneuropathy, Refsum disease)

VI. Syndrome of Progressive Blindness e.g., Optic neuropathy, retinitis pigmentosa, Stargardt disease, diabetic retinopathy, macular degeneration, glaucoma, progressive external ophthalmoplegia with or without other system atrophies)

VII. Syndromes Characterized by Neurosensory Deafness (e.g., pure neurosensory deafness, hereditary hearing loss with retinal diseases, hereditary hearing loss with system atrophies of the nervous system.)

At the molecular level, the possible causes of neurodegeneration are diverse. Glutamate and glycine-induced excitotoxicity and nitric oxide toxicity are all implicated as possible causes of neural cell death, although these very agents are released from already injured cells. Many neurodegenerative conditions are associated, either primarily or secondarily, with ischemia, although other conditions appear to involve ischemia, if at all, as a result of neural injury, rather than as a causal factor.

Furthermore, while not classified as a neurodegenerative disorder, Gaucher disease is, strictly speaking, a disorder of lipid storage, which may have neural sequelae. There are three types of Gaucher disease, and all are characterized by a genetic deficiency in the enzyme glucocerebrosidase, which is responsible for the recycling of the glycolipid glucocerebroside into the sugar glucose and the lipid ceramide. In affected individuals, macrophages lacking a functional glucocerebrosidase accumulate glucocerebroside in their lysozymes, and can be identified microscopically by their distended shape. These cells are characteristic of the disorder, and known as Gaucher cells. Gaucher cells gather in the spleen (causing spleen overactivity, anemia, and leukocytopenia), the liver (occasionally causing scarring of the liver), and bone marrow (where they may interfere with blood cell production and cause brittleness of the bone tissue). Gaucher cells can also be observed accumulating in neural tissue.

The iminosugar-like molecule N-butyl-1-deoxy-nojirimycin (NB-DNJ) is currently approved for use in Europe and the United States for the treatment of mild to moderate Gaucher disease under the trade name Zavesca®. NB-DNJ is an inhibitor of the glycolipid pathway enzyme ceramide specific glucosylceramide transferase. Inhibition of this enzyme prevents the accumulation of sphingolipids involved in the synthesis of glucocerebroside, and thus prevents the accumulation of this glycolipid in macrophages.

More recently, NB-DNJ has been shown to inhibit normal mammal spermatogenesis at concentrations less than those shown to be effective in the treatment of Gaucher disease; sperm cells have a high lipid content, and glycosphingolipids are involved in spermatogenesis. See, e.g., van der Spoel, Aarnoud C. et al., *Proc. Natl. Acad. Sci.* 99:17173 (Dec. 23, 2002).

SUMMARY OF THE INVENTION

The present invention is related to the finding that certain iminosugars, iminosugar derivatives, and structurally related compounds are effective agents in the treatment of chronic pain and neurodegeneration. Preferred compounds include, without limitation, N-butyl-1-deoxy-nojirimycin (NB-DNJ), D-glucaro-delta-lactam, and N-ethyl-1-deoxynojirimycin (NE-DNJ), whose structures are given below.

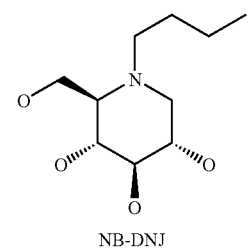

NB-DNJ

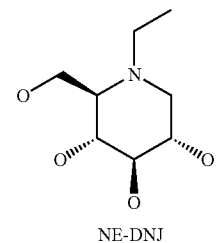

NE-DNJ

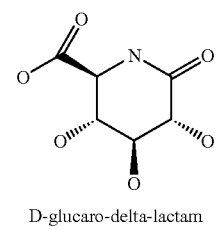

D-glucaro-delta-lactam

Significantly, the finding that iminosugars are useful in the treatment of pain, particularly chronic pain, appears to be unrelated to inhibition of ceramide specific glucosylceramide transferase. Thus, while certain of the compounds whose use as analgesic and neuroprotective agents is claimed herein may inhibit ceramide specific glucosylceramide transferase, other such compounds, active for the uses claimed herein may not. Thus, while not wishing to be bound by theory, Applicants do not currently believe there exists a causal correlation between enzyme inhibition and analgesic or neuroprotective activity.

Therefore, in one aspect the present invention comprises a method of treating or preventing chronic pain, comprising administering to a human a therapeutically effective amount of a compound selected from the group consisting of NB-DNJ and iminosugars having structural similarity to NB-DNJ.

Other iminosugars having structural similarity to NB-DNJ include, without limitation, compounds of the following structures:

Compound 1
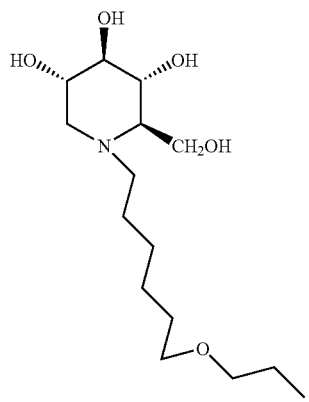

Compound 2
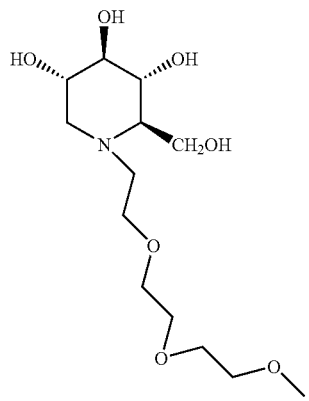

Compound 3
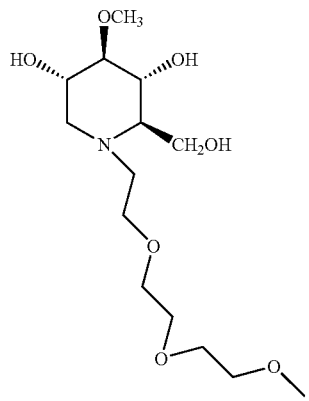

Compound 4
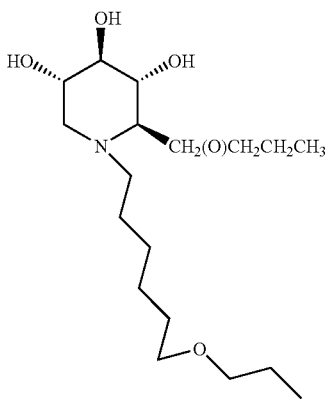

-continued

Compound 5
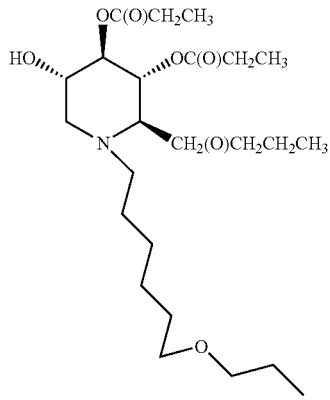

In a preferred embodiment, the compound of this aspect of the invention comprises a compound selected from the group consisting of N-butyl-1-deoxynojirimycin (NB-DNJ), D-glucaro-delta-lactam, and N-ethyl-1-deoxynojirimycin (NE-DNJ).

Applicants have also discovered that certain derivatives of NB-DNJ, having varying amounts of ceramide specific glucosylceramide transferase inhibitory activity, do not have activity in mouse and rat models of chronic pain. Thus, for example, the compound N-butyldeoxygalactonojirimycin (NB-DGJ) was found not to be active in models of chronic pain even though it is reported to be an effective inhibitor of ceramide-specific glucosyltransferase.

Thus, in another embodiment of the invention, the invention comprises a method of using an iminosugars having structural similarity to NB-DNJ for the treatment of chronic pain, with the proviso that such compound does not include N-butyldeoxynojirimycin, N-5-carboxyl-1-deoxynojirimycin, N-dodecyl-1-deoxynojirimycin, nojirimycin bisulfate, nojirimycin-1-sulfonic acid, N-(n-nonyl)-1-deoxynojirimycin, N-(7-oxadecyl)-1-deoxynojirimycin, and N-(7-oxa-9,9,9,-trifluorononyl)-1-deoxynojirimycin, or N-butyldeoxygalactonojirimycin.

The present inventors have also found that compounds having activities similar or identical to NB-DNJ in models of allodynic pain are effective in treating numerous neurological conditions. Thus, the Applicants believe that the present compounds are also useful in the treatment of neurological and neurodegenerative disorders, including, without limitation, Alzheimer's disease, Parkinson's syndrome, non-Alzheimer's dementia, multiple sclerosis, ALS, spasticity and the like, as well as ophthalmological conditions such as, without limitation, diabetic retinopathy, macular degeneration (including age-related macular degeneration), glaucoma, retinitis pigmentosa, macular edema, and the like. All of the above conditions are intended to be included within the meaning of the terms neurodegenerative disorder, neurodegenerative condition, or neurodegenerative disease.

Therefore, in another aspect, the invention is directed to a method of treating or preventing a neurodegenerative disease, comprising administering to a human a therapeutically effective amount of a compound selected from the group consisting of NB-DNJ and iminosugars having structural similarity to NB-DNJ.

In a preferred aspect of this embodiment of the invention, the invention is directed to a method of treating or preventing a neurodegenerative disease, comprising administering to a human a therapeutically effective amount of a compound selected from the group consisting of NB-DNJ and iminosugars having structural similarity to NB-DNJ, and wherein said compound is not N-butyldeoxynojirimycin, N-5-carboxyl-1-deoxynojirimycin, N-dodecyl-1-deoxynojirimycin, nojirimycin bisulfate, nojirimycin-1-sulfonic acid, N-(n-nonyl)-1-deoxynojirimycin, N-(7-oxadecyl)-1-deoxynojirimycin, and N-(7-oxa-9,9,9,-trifluorononyl)-1-deoxynojirimycin, or N-butyldeoxygalactonojirimycin.

Also encompassed within the scope of the invention disclosed herein is a composition comprising a therapeutically effective amount of a compound comprising an iminosugar having structural similarity to NB-DNJ and a pharmaceutically acceptable excipient. Preferably, in this embodiment of the invention the compound is not NB-DNJ, N-butyldeoxynojirimycin, N-5-carboxyl-1-deoxynojirimycin, N-dodecyl-1-deoxynojirimycin, nojirimycin bisulfate, nojirimycin-1-sulfonic acid, N-(n-nonyl)-1-deoxynojirimycin, N-(7-oxadecyl)-1-deoxynojirimycin, and N-(7-oxa-9,9,9,-trifluorononyl)-1-deoxynojirimycin, or N-butyldeoxygalactonojirimycin.

Other embodiments of the invention are disclosed in the descriptions which follow.

BRIEF DESCRIPTION OF THE DRAWINGS

FIG. 5 shows the degree of allodynic reversal upon intraperitoneal administration of different doses of nojirimycin derivatives in the Chung model.

DETAILED DESCRIPTION OF THE INVENTION

Figure 1:
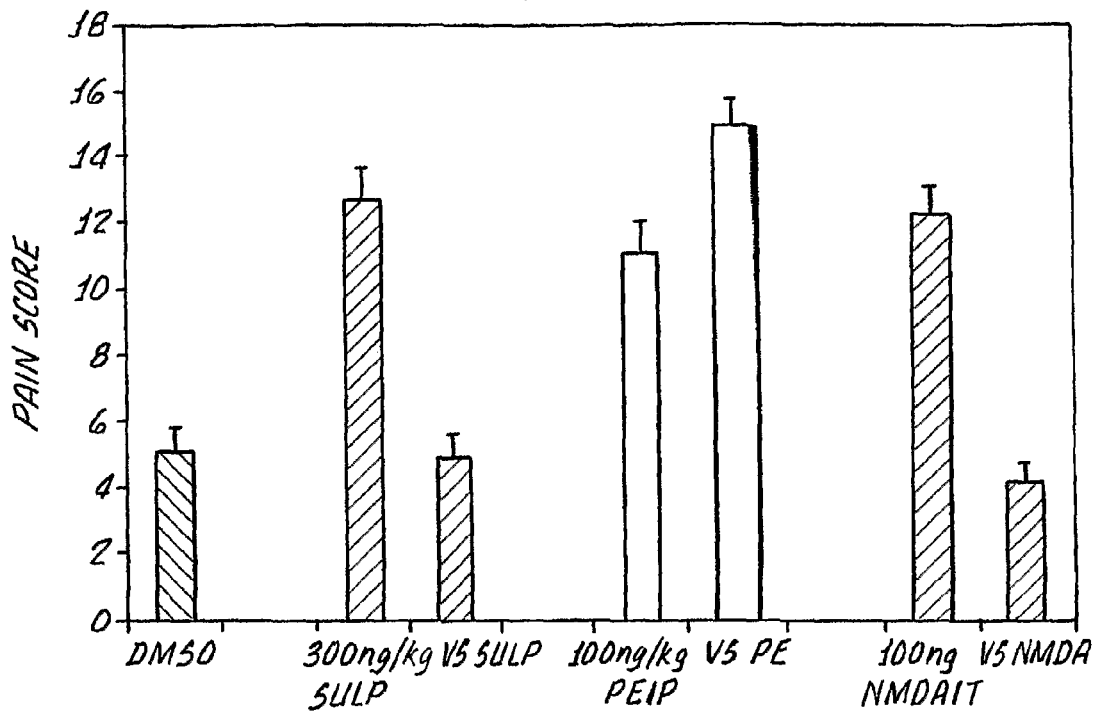
FIG. 1 shows the effect of 1 mg/kg NB-DNJ on reduction of induced allodynia in the mouse pain model. Allodynic agents include sulprostone, NMDA (N-methyl-D-aspartate), and phenylephrine (PE).

The present invention is based upon the finding that NB-DNJ and other compounds having structural similarly to NB-DNJ are active in models of allodynic pain. These compounds show little or no sedative activity, bradycardia, or respiratory depression at doses effective for analgesia or at doses effective for the treatment or prevention of neurodegenerative disorders.

Based on previous findings with other compounds having this activity profile, it is also strongly anticipated that compounds active in the treatment of chronic pain are also effective in the treatment of ophthalmological conditions such as glaucoma, diabetic retinopathy, macular degeneration, macular edema, and the like.

In analgesic and other applications, preferred routes of administration may be peripheral or non-peripheral and include oral, intravenous, intrathecal and epidural administration. Other possible means of administration include, without limitation, by intrathecal pump, subcutaneous pump, dermal patch, intravenous injection, subcutaneous injection, intramuscular injection, topical cream or gel, or an oral pill, eye drops, or a combination of such methods.

As used herein, the term "pain" encompasses both acute and chronic pain. As used herein, the term "acute pain" means immediate, generally high threshold, pain brought about by injury such as a cut, crush, burn, or by chemical stimulation such as that experienced upon exposure to capsaicin, the active ingredient in chili peppers.

In one embodiment the presently claimed methods are directed to the treatment of pain. In a preferred embodiment the invention is directed to the treatment of chronic pain.

The term "chronic pain," as used herein, means pain other than acute pain and includes, without limitation, neuropathic pain, visceral pain, fibromyalgia pain, inflammatory pain, headache pain, muscle pain, referred pain, cancer pain, post-operative pain, post-herpetic neuralgia, gastrointestinal pain (such as irritable bowel syndrome (IBS) and Crohn's disease), diabetic neuropathy, pain associated with muscle spasticity, complex regional pain syndrome (CRPS), sympathetically maintained pain, allodynic pain, and inflammatory pain, such as that associated with arthritis. It is understood that chronic pain is of relatively long duration, for example, a matter of days, months or years, and can be continuous or intermittent.

In one embodiment, the methods of the invention are used to treat "neuropathic pain," which, as used herein, means pain resulting from injury to a nerve. Neuropathic pain can be distinguished from nociceptive pain, which is pain caused by acute tissue injury involving small cutaneous nerves or small nerves in muscle or connective tissue. In contrast to neuropathic pain, nociceptive pain usually is limited in duration to the period of tissue repair and usually can be alleviated by available analgesic agents or opioids (Myers, Regional Anesthesia 20:173-184 (1995)).

Neuropathic pain typically is long-lasting and can develop days or months following an initial acute tissue injury. Neuropathic pain can involve persistent, spontaneous pain, as well as allodynia, which is a painful response to a stimulus that normally is not painful, or hyperalgesia, an accentuated response to a painful stimulus that usually is trivial, such as a pin prick. Neuropathic pain generally is resistant to opioid therapy.

The methods of the invention are useful for treating neuropathic pain resulting from, without limitation, a trauma, injury or disease of peripheral nerve, dorsal root ganglia, spinal cord, brainstem, thalamus or cortex. Examples of neuropathic pain that can be treated by the methods of the invention include neuralgia such as post-herpetic neuralgia, deafferentation pain and diabetic neuropathy. It is understood that the methods of the invention are useful in treating neuropathic pain regardless of the etiology of the pain. As non-limiting examples, the methods of the invention can be used to treat neuropathic pain resulting from a peripheral nerve disorder such as neuroma; from nerve compression; from nerve crush or stretch or incomplete nerve transection; or from a mononeuropathy or polyneuropathy. As further non-limiting examples, the methods of the invention are useful in treating neuropathic pain resulting from a disorder such as dorsal root ganglion compression; inflammation of the spinal cord; contusion, tumor or hemisection of the spinal cord; and tumors or trauma of the brainstem, thalamus or cortex.

As indicated above, the methods of the invention can be useful for treating neuropathic pain resulting from a mononeuropathy or polyneuropathy. A neuropathy is a functional disturbance or pathological change in the peripheral nervous system and is characterized clinically by sensory or motor neuron abnormalities. The term mononeuropathy indicates that a single peripheral nerve is affected, while the term polyneuropathy indicates that several peripheral nerves are affected. The etiology of a neuropathy can be known or unknown. Known etiologies include complications of a disease or toxic state such as diabetes, which is the most common metabolic disorder causing neuropathy, or irradiation, ischemia or vasculitis. Polyneuropathies that can be treated by a method of the invention can result, without limitation, from post-polio syndrome, diabetes, alcohol, amyloid, toxins, HIV, hypothyroidism, uremia, vitamin deficiencies, chemotherapy, 2',3'-dideoxycytidine (ddC) treatment or Fabry's disease. It is understood that the methods of the invention can be used to treat chronic pain of these or other chronic neuropathies of known or unknown etiology.

The methods of the invention also can be used for treating chronic pain resulting from headache, including tension-type headache, migraine headache, cluster headache, hormone headache, rebound headache, sinus headache, and organic headache. The methods of the invention further can be used for treating chronic pain resulting from activity, such as, as non-limiting examples, long hours of work at a computer, work with heavy objects or heavy machinery, or spending long hours on one's feet, and repetitive motion disorders (RMDs). RMDs are a variety of muscular conditions that can cause chronic pain. RMDs can be caused by overexertion, incorrect posture, muscle fatigue, compression of nerves or tissue, too many uninterrupted repetitions of an activity or motion, or friction caused by an unnatural or awkward motion such as twisting the arm or wrist. Common RMDs occur in the hands, wrists, elbows, shoulders, neck, back, hips, knees, feet, legs, and ankles, however, the hands and arms are most often affected. The methods of the invention can be used to treat chronic pain arising from any type of RMD.

The methods of the invention further can used for treating chronic pain resulting from excessive muscle tension, such as certain types of back pain, such as that resulting from a herniated disc; sciatica and joint pain, as well as chronic pain resulting from inflammation, including inflammation caused by an inflammatory disorder such as osteo- and rheumatoid arthritis; inflammation caused by injury, such as a crush, puncture, stretch of a tissue or joint; inflammation caused by infection, such as tuberculosis; or neurogenic inflammation. As non-limiting examples, the methods of the invention can be used to treat chronic gastrointestinal inflammations including Crohn's disease, ulcerative colitis, gastritis, irritable bowel disease and chronic visceral pain such as pain caused by cancer or attendant to the treatment of cancer, for example, attendant to chemotherapy or radiation therapy. Similarly, the methods of the invention can be used to treat chronic inflammatory pain resulting, for example, from arthritis such as rheumatoid arthritis, gouty arthritis, or osteoarthritis; spondylitis; or autoimmune diseases such as lupus erythematosus. The methods of the invention further can be used to treat chronic muscle pain, chronic pain associated with substance abuse or withdrawal, and other types of chronic pain of known or unknown etiology.

In addition to treating pain, particularly chronic pain, the disclosed compounds are also useful for treating stress-associated conditions. Such conditions include, without limitation, sensory hypersensitivity, for example, sensory hypersensitivity (in addition to, or other than pain) associated with fibromyalgia or headache such as migraine; gastrointestinal diseases such as irritable bowel syndrome and dyspepsia; disorders of muscle contraction including disorders of skeletal muscle contraction, disorders of smooth muscle contraction, spasticity, and disorders of muscle contraction associated with tension-type headache.

By reducing or preventing neuronal death, an improvement in pathophysiology or symptoms can be appreciated. As used herein, the term "neuronal death" means destruction of a nerve cell resulting from induction of death in response to an insult or abnormality. Not included in the definition of "neuronal death" is non-pathological neuronal apoptosis, such as that which occurs during embryonic development or in self-renewing tissues containing apoptosis-liable neurons, such as the olfactory epithelium. Therefore, the term neuronal death can include non-olfactory neuroepithelial neuronal damage, such as damage of central nervous system neurons such as brain neurons and neuronal damage within non-apoptosis-liable neurons. As used herein, the term "reducing," when used in reference to neuronal death means preventing, decreasing or eliminating the induction of death in a nerve cell.

As used herein, the term "neurodegenerative condition" means a disorder characterized by progressive nervous system dysfunction. Neurodegenerative conditions include a heterogeneous group of diseases of the central or peripheral nervous system that have many different etiologies. Such conditions can be, without limitation, hereditary, secondary to toxic or metabolic processes, and can result from infection. Neurodegenerative conditions are progressive conditions that can be age associated or chronic. Such conditions can be characterized by abnormalities of relatively specific regions of the brain or specific populations of neurons. The particular cell groups affected in different neurodegenerative conditions typically determine the clinical phenotype of the condition. In particular, neurodegenerative conditions can be associated with atrophy of a particular affected central or peripheral nervous system structure.

Exemplary neurodegenerative conditions include, but are not limited to, Motor Neuron Disease (ALS), Parkinsonian Syndromes, multiple sclerosis, diffuse cerebral cortical atrophy, Lewy-body dementia, Pick disease, mesolimbocortical dementia, thalamic degeneration, bulbar palsy, Huntington chorea, cortical-striatal-spinal degeneration, cortical-basal ganglionic degeneration, cerebrocerebellar degeneration, familial dementia with spastic paraparesis, polyglucosan body disease, Shy-Drager syndrome, olivopontocerebellar atrophy, progressive supranuclear palsy, dystonia musculorum deformans, Hallervorden-Spatz disease, Meige syndrome, familial tremors, Gilles de la Tourette syndrome, acanthocytic chorea, Friedreich ataxia, Holmes familial cortical cerebellar atrophy, AIDS related dementia, Gerstmann-Straussler-Scheinker disease, progressive spinal muscular atrophy, progressive bulbar palsy, primary lateral sclerosis, hereditary muscular atrophy, spastic paraplegia, peroneal muscular atrophy, hypertrophic interstitial polyneuropathy, heredopathia atactica polyneuritiformis, optic neuropathy, diabetic retinopathy, Alzheimer's disease and ophthalmoplegia. The skilled person understands that these and other mild, moderate or severe neurodegenerative conditions can be treated according to a method of the invention.

Examples of ocular conditions that can be treated using a method of the invention include, but are not limited to, glaucoma, including open angle glaucoma, ocular hypertension, maculopathies and retinal degeneration, such as Non-Exudative Age Related Macular Degeneration (ARMD), Exudative Age Related Macular Degeneration (ARMD), Choroidal Neovascularization, Diabetic Retinopathy, Central Serous Chorioretinopathy, Cystoid Macular Edema, Diabetic Macular Edema, Myopic Retinal Degeneration; inflammatory diseases, such as Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpiginous Choroiditis, Subretinal Fibrosis and Uveitis Syndrome, Vogt-Koyanagi-Harada Syndrome, Punctate Inner Choroidopathy, Acute Posterior Multifocal Placoid Pigment Epitheliopathy, Acute Retinal Pigment Epitheliitis, Acute Macular Neuroretinopathy; vascular and exudative diseases, such as Diabetic retinopathy, Central Retinal Arterial Occlusive Disease, Central Retinal Vein Occlusion, Disseminated Intravascular Coagulopathy, Branch Retinal Vein Occlusion, Hypertensive Fundus Changes, Ocular Ischemic Syndrome, Retinal Arterial Microaneurysms, Coat's Disease, Parafoveal Telangiectasis, Hemi-Retinal Vein Occlusion, Papillophlebitis, Central Retinal Artery Occlusion, Branch Retinal Artery Occlusion, Carotid Artery Disease (CAD), Frosted Branch Angiitis, Sickle Cell Retinopathy and other Hemoglobinopathies, Angioid Streaks, Familial Exudative Vitreoretinopathy; Eales Disease; traumatic, surgical and environmental disorders, such as Sympathetic Ophthalmia, Uveitic Retinal Disease, Retinal Detachment, Trauma, Retinal Laser, Photodynamic therapy, Photocoagulation, Hypoperfusion During Surgery, Radiation Retinopathy, Bone Marrow Transplant Retinopathy; proliferative disorders, such as Proliferative Vitreal Retinopathy and Epiretinal Membranes; infectious disorders, such as Ocular Histoplasmosis, Ocular Toxocariasis, Presumed Ocular Histoplasmosis Syndrome (POHS), Endophthalmitis, Toxoplasmosis, Retinal Diseases Associated with HIV Infection, Choroidal Disease Associate with HIV Infection, Uveitic Disease Associate with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis; genetic disorders, such as Retinitis Pigmentosa, Systemic Disorders with Associated Retinal Dystrophies, Congenital Stationary Night Blindness, Cone Dystrophies, Stargardt's Disease And Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum; retinal injuries, such as Macular Hole, Giant Retinal Tear; retinal tumors, such as Retinal Disease Associated With Tumors, Congenital Hypertrophy Of The RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, and Intraocular Lymphoid Tumors.

Ischemia of the neuroretina and optic nerve can arise during retinal branch vein occlusion, retinal branch artery occlusion, central retinal artery occlusion, central retinal vein occlusion, during intravitreal surgery, in retinal degenerations such as retinitis pigmentosa, and age-related macular degeneration.

The ability of the compositions used in the methods of the present invention to reduce neuronal death or dysfunction can be assessed by analyzing an observable sign or symptom of nerve cell destruction in the presence and absence of treatment with the compound. Initiation of apoptotic death of neurons can have observable effects on cell function and morphology, as well as observable effects on tissues, organs and animals that contain dysfunctional or apoptotic neurons. Therefore, an indicator of neuronal damage can include observable parameters of molecular changes, such as increased expression of apoptosis-induced genes; cell function changes, such as reduced mitochondrial functions; cell morphological changes, such as cell shrinkage and blebbing; organ and tissue functional and morphological changes, such as the presence of an infarct or other lesion, the severity of which can be assessed by parameters including lesion volume and lesion size; physiological changes in animal models, including functional changes, such as loss of motor function, increased mortality and decreased survival, and behavioral changes, such as onset of dementia or loss of memory.

A reduction in an indicator of neuronal damage can be assessed in a cell, tissue, organ or animal by comparing an indicator of neuronal damage in at least two states of a cell, tissue, organ or animal. Thus, a reduction in an indicator of neuronal damage can be expressed relative to a control condition. A control condition can be, for example, a cell, tissue, organ or animal prior to treatment, in the absence of treatment, in the presence of a different treatment, in a normal animal or another condition determined to be appropriate by one skilled in the art.

In particular embodiments, a method of the invention is practiced by peripheral administration of a compound as disclosed herein. As used herein, the term "peripheral administration" or "administered peripherally" means introducing an agent into a subject outside of the central nervous system. Peripheral administration encompasses any route of administration other than direct administration to the spine or brain. As such, it is clear that intrathecal and epidural administration as well as cranial injection or implantation, while within the scope of embodiments of the invention, are not within the scope of the terms "peripheral administration" or "administered peripherally."

Peripheral administration can be local or systemic. Local administration results in significantly more of a pharmaceutical composition being delivered to the site of local administration than to regions distal to the site of administration. Systemic administration results in delivery of a pharmaceutical composition to essentially the entire peripheral nervous system of the subject and can also result in delivery to the central nervous system depending on the properties of the composition.

Routes of peripheral administration useful in the methods of the invention encompass, without limitation, oral administration, topical administration, intraocular administration, intravenous or other injection, and implanted minipumps or other extended release devices or formulations. A pharmaceutical composition useful in the invention can be peripherally administered, for example, orally in any acceptable form such as in a tablet, liquid, capsule, powder, or the like; by intravenous, intraperitoneal, intramuscular, subcutaneous or parenteral injection; by transdermal diffusion or electrophoresis; topically in any acceptable form such as in drops, creams, gels or ointments; and by minipump or other implanted extended release device or formulation.

Of course, whether peripheral or non-peripherally administered the presently disclosed compounds may be administered in any manner suitable for the precise condition being treated, and may include, oral (as a tablet, capsule or liquid), intravenous, intraperitoneal, intrarectal, intrathecal, or, particularly or ophthalmic administration, as a topical or intraocular formulation. Intraocular formulations may include injection or implantation within a solid device.

Formulations can be made, and dosages determined, based on the solubility and bioavailability of the chosen compound, and the mode of administration. Preferred administration modes for the treatment of pain are oral and intravenous.

Oral administration of NB-DNJ or compounds structurally similar to NB-DNJ is well-known in the art. NB-DNJ (which is also known as miglustat) is sold under the trade name Zavesca®. Zavesca® is 100 mg NB-DNJ contained in a hard gelatin capsule as a powder, with povidone (K30), sodium starch glycolate, and magnesium stearate. NB-DNJ has an aqueous solubility of greater than 1000 mg/ml.

Of course, other oral formulations of NB-DNJ or compounds structurally similar to NB-DNJ can easily be made by a person of ordinary skill in the art. Thus, solid dosage forms, including, without limitation, tablets, powders, liquids, or soft gelatin capsules can be made such that a therapeutically effective dose may be provided. See, e.g., *Remington's Pharmaceutical Sciences*, Mack Publishing Company, Easton, Pa., 16th Edition, 1980, hereby incorporated by reference herein.

Of course, any suitable method of administering the presently useful compound or compounds to a mammal to be treated may be used. In all the methods, the preferred mammal is a human. The particular method of administration chosen is preferably one which allows the presently useful compound or compounds to have the desired therapeutic effect in an effective manner, e.g., low effective concentration and low incidence of side effects.

Other means of administration of the presently useful compounds for use in the methods of this invention can include, but are not limited to, parenteral, intravenous, subcutaneous, transdermal, rectal and other modes of systemic administration. The compounds are administered in a therapeutically effective amount either alone or in combination with a suitable pharmaceutically acceptable carrier or excipient.

Depending on the intended mode of administration, the presently useful compound or compounds may be incorporated in any pharmaceutically acceptable dosage form, such as for example, tablets, suppositories, pills, transdermal patches, capsules, powders, liquids, solutions, infusions, suspensions, emulsions, aerosols or the like, preferably dosage forms suitable for single administration of precise dosages, or sustained release dosage forms for continuous controlled administration. Preferably, the dosage form will include a pharmaceutically acceptable excipient and the presently useful compound or compounds and, in addition, may contain other medicinal agents, pharmaceutical agents, carriers, adjutants, etc.

For solid dosage forms, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. An example of a solid dosage form for carrying out the invention is a suppository containing propylene glycol as the carrier.

Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see *Remington's Pharmaceutical Sciences*, Mack Publishing Company, Easton, Pa., 16th Edition, 1980, incorporated by reference herein. The composition of the formulation to be administered, in any event, contains a quantity of one or more of the presently useful compounds in an amount effective to provide the desired therapeutic effect.

Parenteral administration is generally characterized by injection, either subcutaneously, intramuscularly or intravenously. Injectables can be prepared in conventional forms, either as liquid solutions or suspensions, solid forms suitable for solution or suspension in liquid prior to injection as emulsions or infusions. Suitable excipients are, for example, water, saline, dextrose, glycerol, ethanol and the like. In addition, if desired, the injectable or infusible pharmaceutical compositions to be administered may also contain minor amounts of non-toxic auxiliary substances such as wetting or emulsifying agents, pH buffering agents and the like.

The amount of the presently useful compound or compounds administered is, of course, dependent on the therapeutic effect or effects desired, on the specific mammal being treated, on the severity and nature of the mammal's condition, on the manner of administration, on the potency and pharmacodynamics of the particular compound or compounds employed, and on the judgment of the prescribing physician. Generally, the therapeutically effective dosage of the presently useful compound or compounds is preferably in the range of about 0.001 to about 500 mg/kg. Even more preferably, the dosage is generally in the range of about 0.01 to about 100 mg/kg.

Biological Models

A) The Chung Model

One standard model for chronic pain involves the surgical ligation of the L5 (and optionally the L6) spinal nerves on one side in experimental animals. Rats recovering from the surgery gain weight and display a level of general activity similar to that of normal rats. However, these rats develop abnormalities of the foot, wherein the hindpaw is moderately everted and the toes are held together. More importantly, the hindpaw on the side affected by the surgery appears to become sensitive to pain from low-threshold mechanical stimuli, such as that producing a faint sensation of touch in a human, within about 1 week following surgery. This sensitivity to normally non-painful touch is called "tactile allodynia" and lasts for at least two months. The response includes lifting the affected hindpaw to escape from the stimulus, licking the paw and holding it in the air for many seconds. None of these responses is normally seen in the control group.

Rats are anesthetized before surgery. The surgical site is shaved and prepared either with betadine or novocaine. Incision is made from the thoracic vertebra XIII down toward the sacrum. Muscle tissue is separated from the spinal vertebra (left side) at the L4-S2 levels. The L6 vertebra is located and the transverse process is carefully removed with a small rongeur to expose the L4-L6 spinal nerves. The L5 and L6 spinal nerves are isolated and tightly ligated with 6-0 silk thread. The same procedure is done on the right side as a control, except no ligation of the spinal nerves is performed.

A complete hemostasis is confirmed, then the wounds are sutured. A small amount of antibiotic ointment is applied to the incised area, and the rat is transferred to the recovery plastic cage under a regulated heat-temperature lamp. On the day of the experiment, at least seven days after the surgery, six rats per test group are administered the test drugs by intraperitoneal (i.p.) injection or oral gavage. For i.p. injection, the compounds are formulated in d-$H_2O$ and given in a volume of 1 ml/kg body weight using an 18-gauge, 3-inch gavage needle that is slowly inserted through the esophagus into the stomach.

Tactile allodynia is measured prior to and 30 minutes after drug administration using von Frey hairs that are a series of fine hairs with incremental differences in stiffness. Rats are placed in a plastic cage with a wire mesh bottom and allowed to acclimate for approximately 30 minutes. The von Frey hairs are applied perpendicularly through the mesh to the mid-plantar region of the rats' hindpaw with sufficient force to cause slight buckling and held for 6-8 seconds. The applied force has been calculated to range from 0.41 to 15.1 grams. If the paw is sharply withdrawn, it is considered a positive response. A normal animal will not respond to stimuli in this range, but a surgically ligated paw will be withdrawn in response to a 1-2 gram hair. The 50% paw withdrawal threshold is determined using the method of Dixon, W. J., *Ann. Rev. Pharmacol. Toxicol.* 20:441-462 (1980), hereby incorporated by reference. The post-drug threshold is compared to the pre-drug threshold and the percent reversal of tactile sensitivity is calculated based on a normal threshold of 15.1 grams.

B) Mouse Sulprostone Model

In this alternative model of chronic pain, allodynia can be induced in mice through intraperitoneal treatment of the animals with 300 ng/kg sulprostone (prostaglandin E2 receptor agonist) in 50% DMSO and in a volume of 5 µl. In this model, the pain response to stroking the flank with a paint brush is scored 8 times over a 35 minute period starting 15 minutes following spinal administration of sulprostone. Minami et al., 57 Pain 217-223 (1994), hereby incorporated by reference herein. Sulprostone treatment alone elicits a score of 12-13 on a 16-point scale.

In variants of this model, allodynia can be induced using 100 ng N-methyl-D-aspartate (NMDA) in DMSO intrathecally, or IP phenylephrine (PE) 100 ng/kg formulated in d$H_2O$.

In either model, the compounds are formulated in d-$H_2O$ and given in a volume of 1 ml/kg body weight for intraperitoneal (IP) dosing.

Chemical Synthesis

I. DNJ: 1-deoxynojirimycin (DNJ) is a naturally occurring sugar, and can be isolated from the roots of *Morus alba*, as set forth in Asano et al., CARBOHYDR. RES. 1994 Jun. 17; 259(2): 243-55. DNJ can also be isolated from the fermentation media of a culture of *Streptomyces lavendulae* as set forth in Tsuruoka et al., SCI. REPORTS MOEIJI SEIKA KAISHA 13:80-84 (1973), both of which are hereby incorporated by reference herein in their entirety.

II. NB-DNJ: 12.5 ml of n-butyraldehyde, 0.01 mols of methanolic HCl and 1.5 g of NaCNBH$_3$ are added successively to 3.2 g of 1-deoxynojirimycin (0.02 mol) in 40 ml of absolute methanol, while cooling with ice and stirring. The reaction mixture is stirred at room temperature for 12 hours. It is then concentrated to dryness on a rotary evaporator. The residue is dissolved in 50 ml of water and extracted 3 times with 30 ml of CHCl$_3$ each time. The aqueous phase is again brought to dryness, the residue is taken up in 30 ml of H$_2$O and the solution is discharged onto a column 50 cm long and 2 cm wide which is filled with a strongly basic ion exchange resin in the OH$^\ominus$ form (Amberlite IRA 400 or Dowex 1X2).

The reaction product is eluted with water and the individual fractions are investigated by thin layer chromatography. (Silica gel plates; running agent: ethyl acetate/methanol/water/25% strength ammonia 100:60:40:2; spray reagent: KMnO$_4$ solution). The fractions which contain N-n-butyl-1-deoxynojirimycin are collected and the aqueous solution is concentrated on a rotary evaporator. Acetone is added to the residue, whereupon crystallization occurs.

The crystals are filtered off, rinsed briefly with acetone and dried. 3 g of N-n-butyl-1-deoxynojirimycin of melting point 126°-127° C. are obtained.

Mass spectrum: The most important peaks in the upper mass range are found at m/e=188 (M—CH$_2$OH) and m/e=176 (M—CH$_2$—CH$_2$—CH$_3$).

In the case of less reactive aldehydes, a molecular sieve 3 A is added to the reaction mixture in order to bind the water of reaction.

III. N-ethyl-deoxynojirimycin: Using an analogous synthetic scheme as employed in II above, N-ethyl-deoxynojirimycin is produced. Mass spectrum reveals an intense peak at m/e=160 (M—CH$_2$OH).

IV. D-Glucaro-Delta-Lactam: Eighteen grams DNJ in 400 ml water is treated alternatively with 1100 ml 0.2 N I$_2$ (110 ml at one time) and 1650 ml 0.2N NaOH (once 165 ml). The additions require about 40 minutes. The reaction mixture is permitted to stand for about 30 minutes, then passed through a column of Amberlite IR-120 (H$^+$, 1 l). The effluent and washings are combined (about 3.8 l) AgCO$_3$ (200 g) is added and stirred for 30 minutes. After filtration, the filtrate is passed through a column of Amberlite IR-120 (H$^+$, 300 ml). The effluent and washings are again combined, neutralized with Amberlite IR-45 (OH—) and evaporated to yield D-gluconic-δ-lactam (II), which is crystallized from water and methanol in a yield of 12.2 g. m.p.=203°-205° C.

In a three necked flask, 3 g of freshly reduced platinum catalyst is suspended in an aqueous solution (400 ml) containing 8.8 g of II. Oxygen is bubbled with vigorous stirring at 65° C. 0.5N NaOH is added as necessary to maintain a pH of 8-9. The reaction is complete in about 3 hours. The mixture is filtered and the filtrate is evaporated to about 30 ml. The concentrate is applied to a carbon column and developed with water Evaporation of effluents containing the sodium salt of D-glucaro-δ-lactam (III) give a white powder. m.p.=185°-190° C. [α]22/D+30° (c 1, H₂O).

The free acid of III is obtained by dissolving III in water, and applying to a column of Amberlite IR-120.

Catalytic oxidation of (II) is carried out using palladium at 60°-70° C. in the presence of an equivalent of sodium hydrogen carbonate or calcium carbonate in weakly alkaline solution for 3 hours.

V. Compounds 1, 2, 3, 4 and 5: Synthesis of these and other useful derivative NB-DNJ based compounds is carried out as described in van den Broek et al., RECL. TRAV. CHIM. PAYS-BAS 113:507-516 (1994), or by using analogous methods. This reference is hereby incorporated by reference herein in its entirety.

For other relevant papers and publications concerning synthesis and structures of NB-DNJ derivatives, see also U.S. Pat. No. 4,260,622; McDonnell et al., J. ORG. CHEM. 69:3565-35-68 (2004); Singh, et al., TETRAHEDRON LETTERS 44:2387-2391 (2003); Butters, et al., Tetrahedron: Asymmetry 11:113-124 (2000), all of which are hereby incorporated by reference herein.

Example 1

Six mice per group are rendered allodynic by injection of one of the following agents: 300 ng/kg sulprostone in DMSO IP, 100 ng/kg phenylephrine (PE) in dH₂O IP, or 100 ng NMDA in DMSO intrathecally (IT). Fifteen minutes before administration of the allodynia-inducing agents, the experimental mice are given 1 mg/kg NB-DNJ. Thirty (30) minutes following administration of NB-DNJ, the allodynic response is monitored as described by brushing the flank of each mouse with a paint brush.

FIG. 1 shows that NB-DNJ provides significant reversal of the allodynic response in the animals made allodynic by administration of sulprostone or NMDA. For the animals given PE, no reversal was observed.

Example 2

Six mice per group are given one of the following: given 100 µg/kg NB-DNJ, 300 µg/kg NB-DNJ, 1 mg/kg NB-DNJ, or 3 mg/kg 1-deoxynojirimycin. After 15 minutes the mice are rendered allodynic by injection of 200 ng NMDA in DMSO IT.

Starting thirty (30) minutes following administration of NB-DNJ, the allodynic response of each mouse is monitored by brushing the flank of the mouse with a paint brush.

Figure 2:
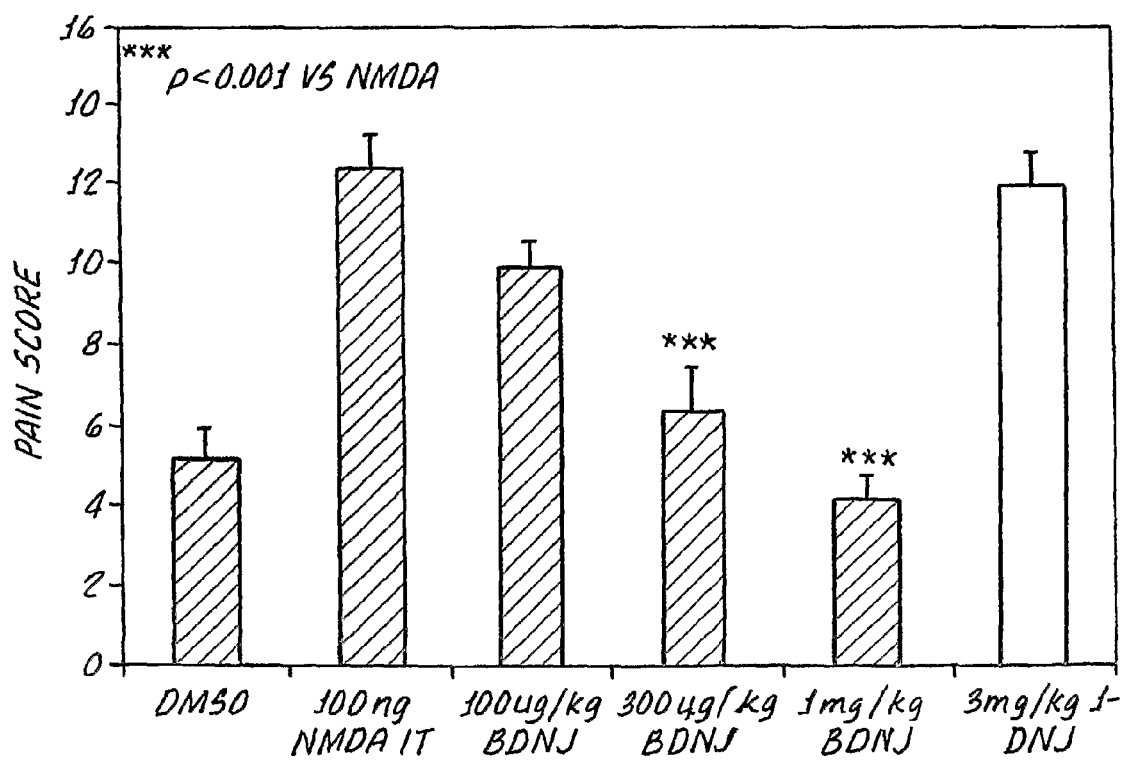
FIG. 2 shows the effect of various dosages of nojirimycin derivatives on pain reduction in the mouse NMDA pain model.

FIG. 2 shows a dose response at different doses of NB-DNJ. The figure also shows that 1-DNJ is not analgesic at a dosage of 3 mg/kg.

Example 3

Five to six mice per group are rendered allodynic by injection of 300 ng/kg sulprostone IP. Fifteen minutes before inducement of an allodynic response, experimental mice are given one of the following: 1 mg/kg, 300 µg/kg, and 100 µg/kg NB-DNJ; 1 mg/kg N-butyldeoxymannojirimycin; 1 mg/kg N-5-carboxy-1-deoxynojirimycin; 1 mg/kg N-dodecyldeoxynojirimycin; 1 mg/kg N-ethyl-1-deoxynojirimycin; 1 mg/kg, 300 µg/kg, and 30 µg/kg D-glucaro-delta-lactam; 1 mg/kg 4-O-a-D-glucopyranosylmoranoline; 1 mg/kg nojirimycin bisulfite; 1 mg/kg nojirimycin-1-sulfonic acid; 1 mg/kg N-(n-nonyl)deoxynojirimycin; 1 mg/kg N(7-oxadecyl)deoxynojirimycin; and 1 mg/kg N-(7-oxa-9,9,9-trifluorononyl)deoxynojirimycin. The DMSO vehicle and sulprostone alone are used as controls.

Starting thirty (30) minutes following administration of NB-DNJ, the allodynic response of each mouse was monitored by brushing the flank of the mouse with a paint brush.

Figure 3:
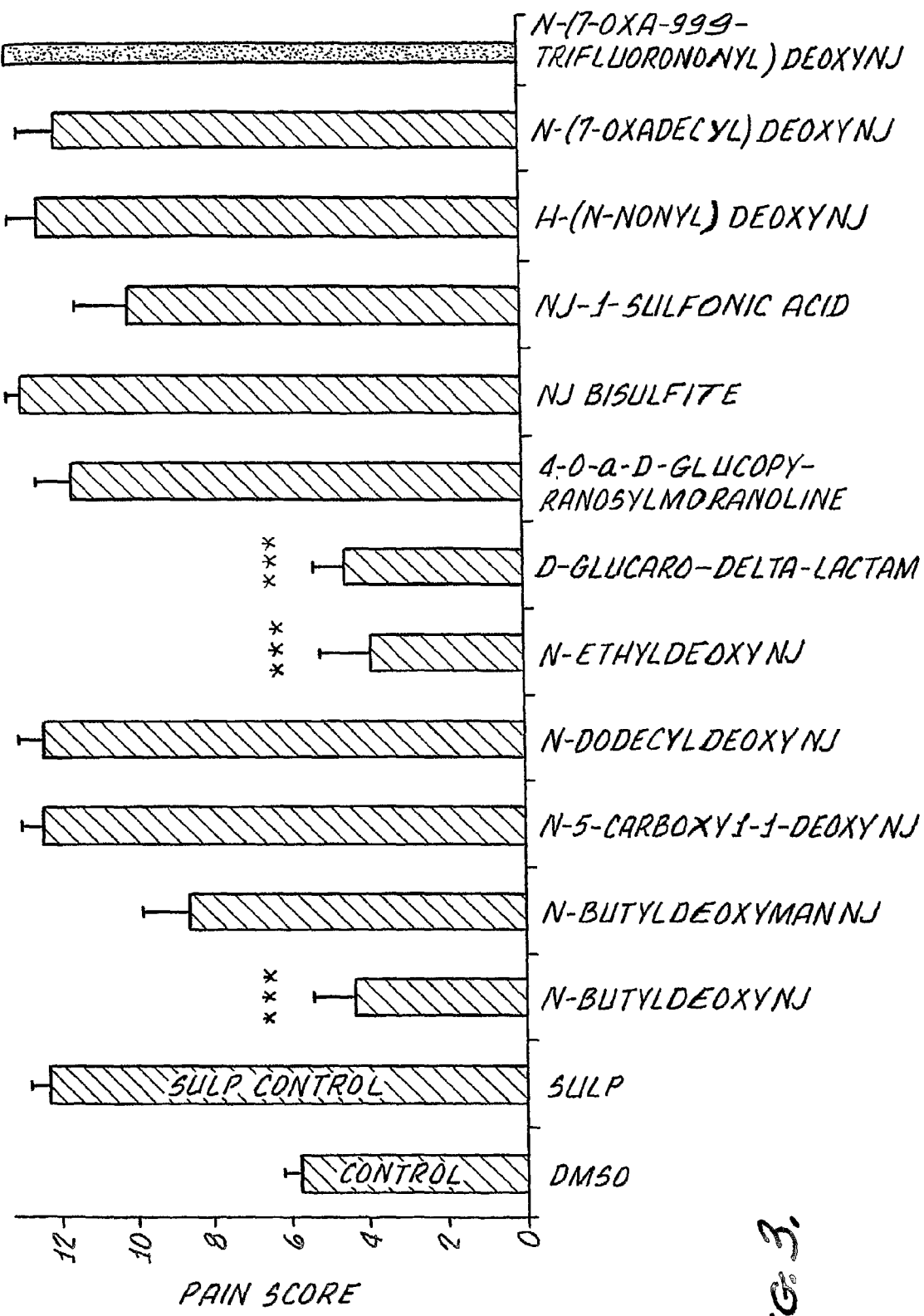
FIG. 3 shows the effect on reversal of allodynic pain of different nojirimycin derivatives in the mouse sulprostone pain model.

As shown in FIG. 3, NB-DNJ, N-ethyldeoxynojirimycin, and D-glucaro-delta-lactam were shown to attenuate the allodynic response in sulprostone-treated mice. The other compounds did not show significant analgesic activity at the dosages tested. None of the compounds show sedation, even at the higher concentrations used.

Example 4

Five to six mice per group are rendered allodynic by injection of one of the following: 300 ng/kg sulprostone IP, 100 ng/kg phenylephrine (PE) IP, or 100 ng NMDA intrathecally (IT). Fifteen minutes prior to the induction of allodynia, the mice are given D-glucaro-delta-lactam IP at 30 g/kg, 100 g/kg, or 1 mg/kg. PE or NMDA-treated mice are given 1 mg/kg D-glucaro-delta-lactam IP.

Figure 4:
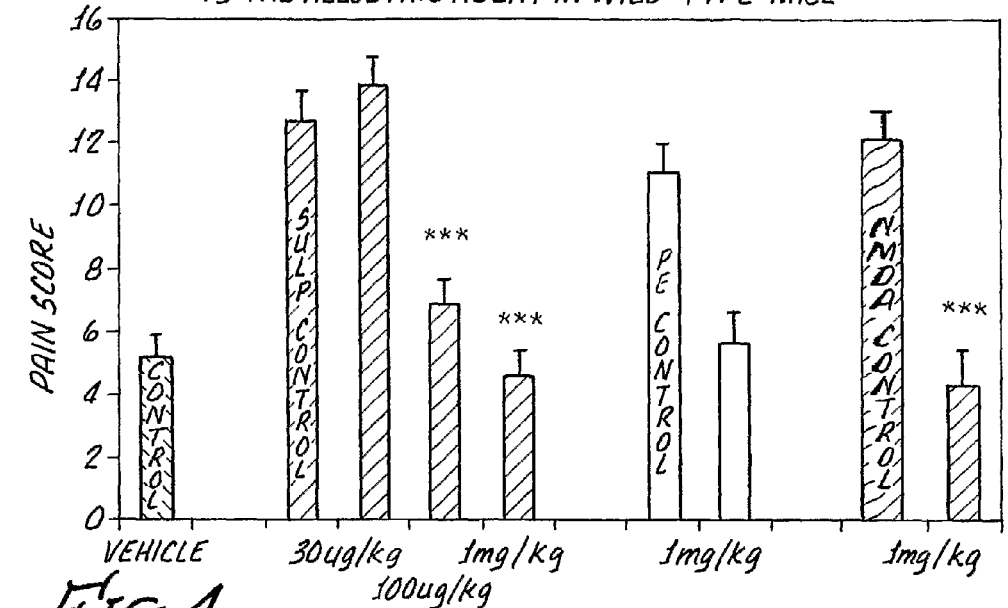
FIG. 4 shows the effect on reversal of allodynic pain of different doses of D-glucaro-delta-lactam in the mouse sulprostone, NMDA, and PE models.

The results, graphically shown in FIG. 4, indicate that D-glucaro-delta-lactam is able to achieve an analgesic effect, regardless of the agent used to induce allodynia.

Example 5

Five to six ligated Chung rats are given one of the following compounds at the indicated dosage: 1 mg/kg NB-DNJ, 3 mg/kg NB-DNJ, 3 mg/kg N-butyldeoxygalactonojirimycin, 3 mg/kg 1-deoxynojirimycin, or 3 mg/kg deoxymannojirimycin intraperitoneally. Control rats are given the vehicle alone. Thirty (30) minutes following administration rats are brushed with Von Freys hairs and tactile allodynia is measured using the method of Dixon, as described above.

As shown in FIG. 5, NB-DNJ is analgesic in the Chung rat model.

Example 6

Five to six ligated Chung rats are given 1 mg/kg D-glucaro-delta-lactam intraperitoneally. Control rats are given the vehicle alone. Thirty (30) minutes following administration rats are brushed with Von Freys hairs and tactile allodynia is measured using the method of Dixon, as described above.

Figure 6:
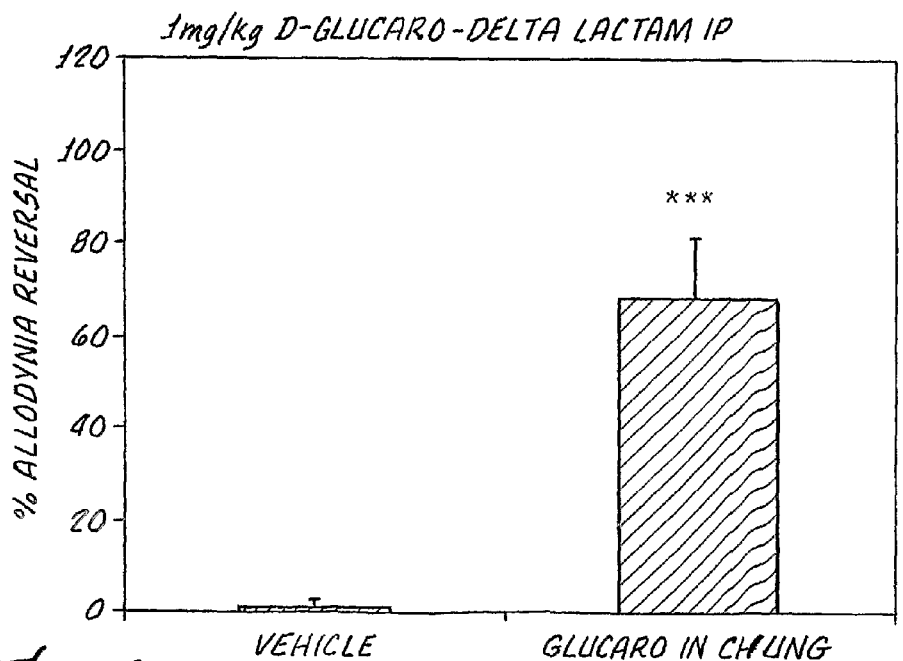
FIG. 6 shows an approximately 70% reversal of induced allodynia upon intraperitoneal administration of 1 mg/kg of the NB-DNJ derivative D-glucaro-delta-lactam in the Chung rat model.

The results, as shown in FIG. 6, demonstrate that the vehicle alone provides the rats no significant relief from allodynic pain. By contrast, rats given 1 mg/kg D-glucaro-delta-lactam have an approximately 70% reduction in allodynic response to Von Freys hair stimulus. Thus, D-glucaro-delta-lactam is shown to be analgesic against chronic pain in the Chung model.

The actual dose of the active compounds of the present invention depends on the specific compound, and on the condition to be treated; the selection of the appropriate dose is well within the knowledge of the skilled artisan.

Example 7

Primary rat brain cortical neurons were cultured as follows. In brief, rat cerebral cortices were removed from brains of the 16 day-old-fetal rats. The neocortices were gently triturated and plated on 24 well plates (300,000 viable cells/cm2) in plating Modified Eagle's Medium (MEM) supplemented with 10% horse serum, 10% fetal calf serum and 2 mM L-glutamine. Cultures were maintained at 37 C in a humidified 5% CO2 atmosphere.

After 4 days' growth (DIV 4), half of the medium was replaced by a medium identical to the plating medium but lacking calf serum. At DIV4, 10 μM 5-fluoro-2-deoxyuridine was included to each well to halt overgrowth of glia. Mixed cultures of neurons and glia were then fed at DIV7 and DIV11 with MEM plus 5% horse serum previously conditioned by growth with cortical astrocytes for 24 h.

Excitotoxicity was induced in these cells by addition of 50 μM kainate or 20 μM N-methyl-D-aspartate plus 10 μM D-serine to each well.

Under the experimental conditions used, i.e. after 6 hours addition of excitotoxic agent, 40% toxicity is generally observed and measured by determination of the amount of lactate dehydrogenase (LDH) released into the medium following membrane degradation. Such assay methods are well-known; a kit for conducting a homogeneous form of the LDH assay format is sold by Promega under the name CytoTox ONE® Homogenous Membrane Integrity Assay. Overall cell injury was assessed microscopically under phase-contrast optics or by measuring amount of LDH released into the bathing medium 24 hr after neurotoxic insults (see, e.g., Koh and Choi, J. NEUROSCI. METHODS 20: 83-90, 1987), hereby incorporated by reference herein.

Experimental neuronal culture treatments were performed as follows: various concentrations of NB-DNJ were added to the wells 18 h before, 3 h before or at the time of addition of the toxic agent. The final results are normalized optical density (OD) values (treated cells/untreated control cells), where a value of 1 represents 100% neuronal survival and a value of 0.6 represents 60% survival.

Figure 7A:
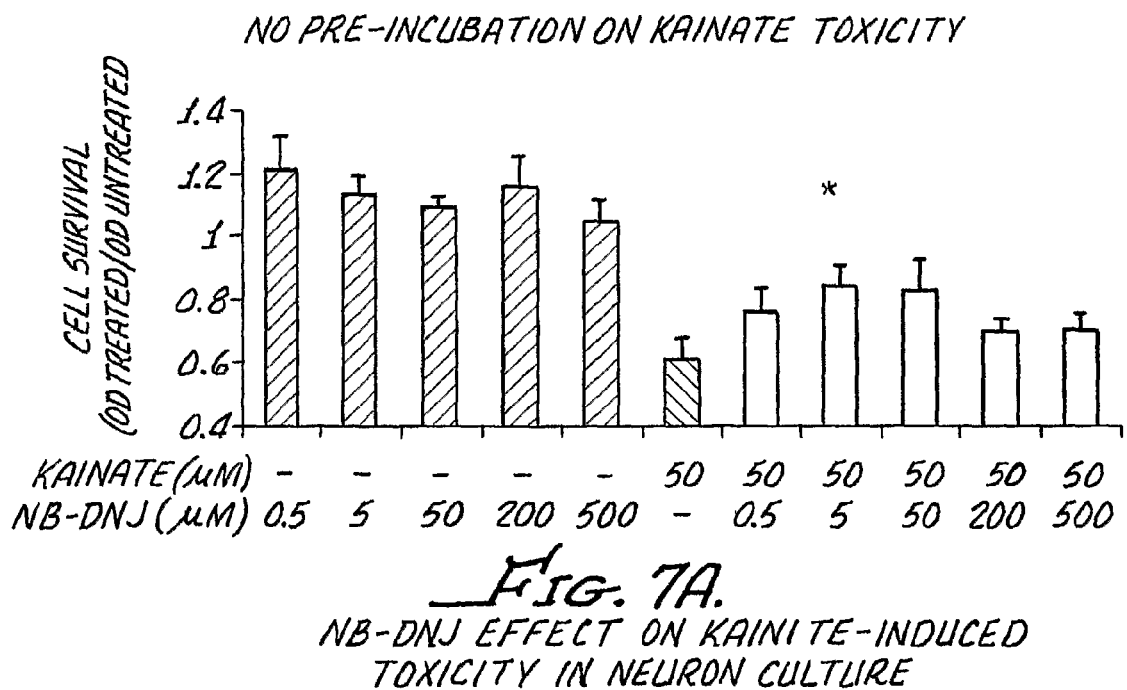
FIG. 7A shows the effect of various doses of NB-DNJ on kainate-treated neural cells in culture.
Figure 7B:
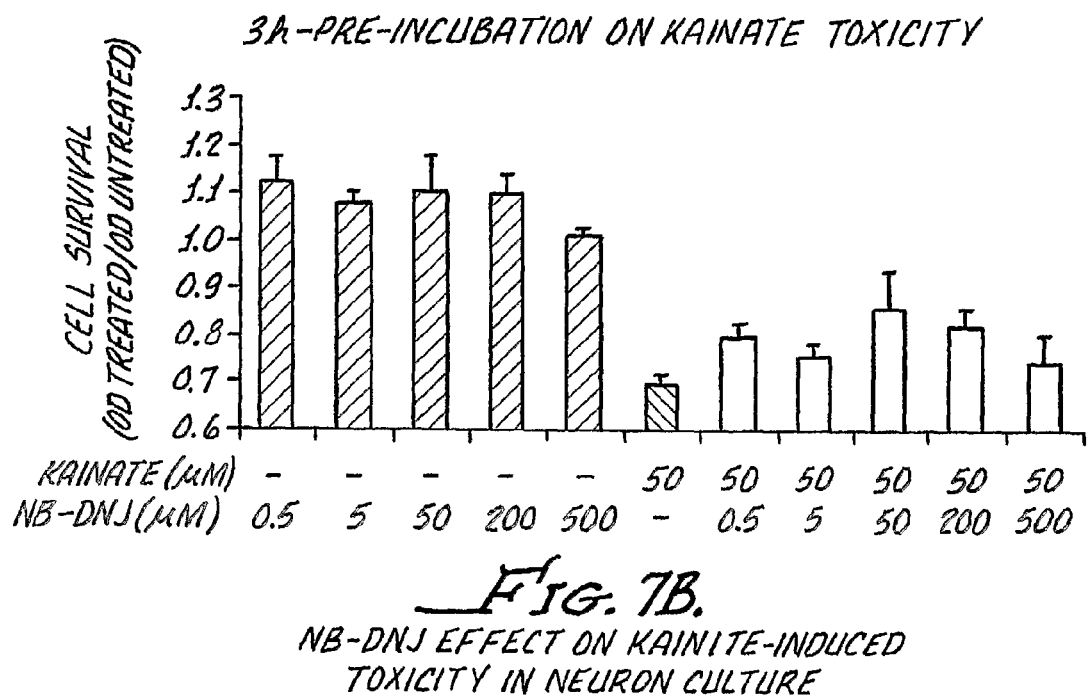
FIG. 7B shows the effect of 3 hours' preincubation with NB-DNJ on neural cells in culture subsequently treated with kainate.
Figure 7C:
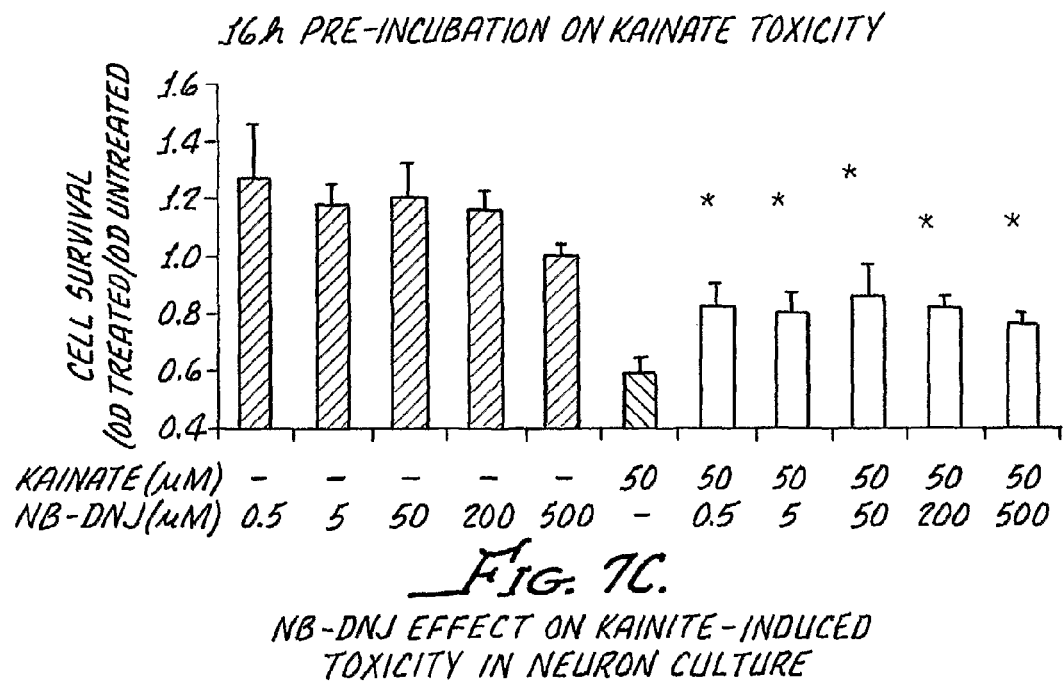
FIG. 7C shows the effect of 16 hours' preincubation with NB-DNJ on neural cells in culture subsequently treated with kainate.

FIG. 7A-7C presents the results obtained after treatment with NB-DNJ. FIG. 7A shows the attenuation of kainate-induced excitotoxicity upon addition of NB-DNJ to the cultures without pre-incubation. FIGS. 7B and 7C show the same trend when cells were pre-incubated with NB-DNJ for 3 hours or 16 hours, respectively.

Figure 8A:
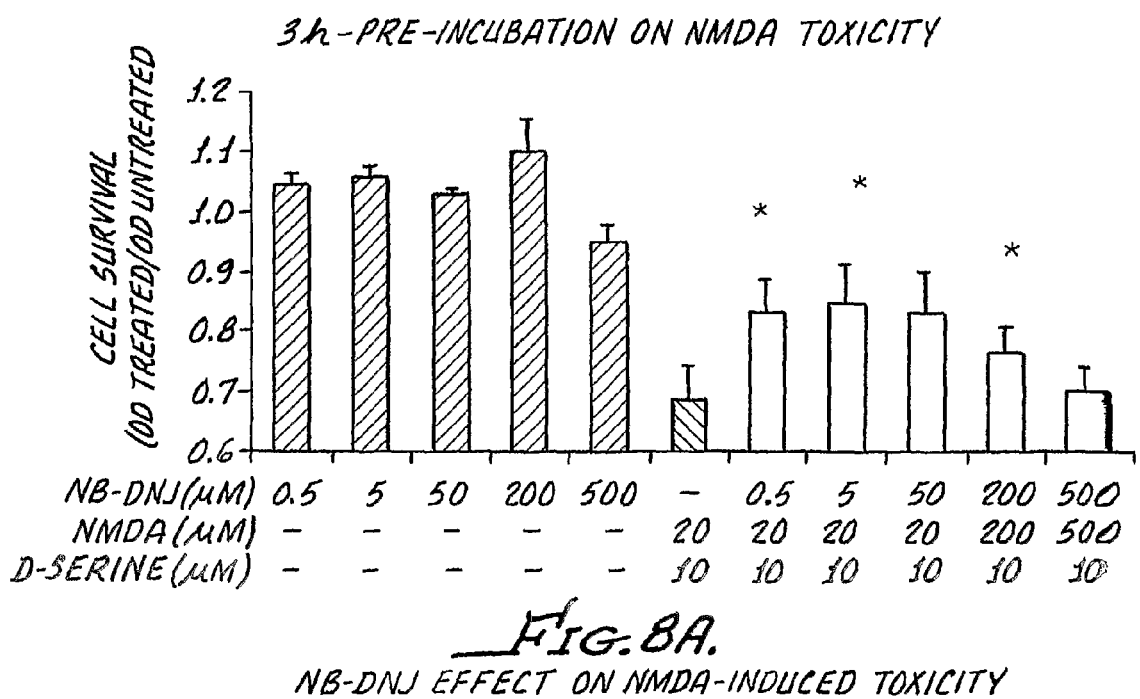
FIG. 8A shows the effect of 3 hours' preincubation with NB-DNJ on neural cells in culture subsequently treated with NMDA.
Figure 8B:
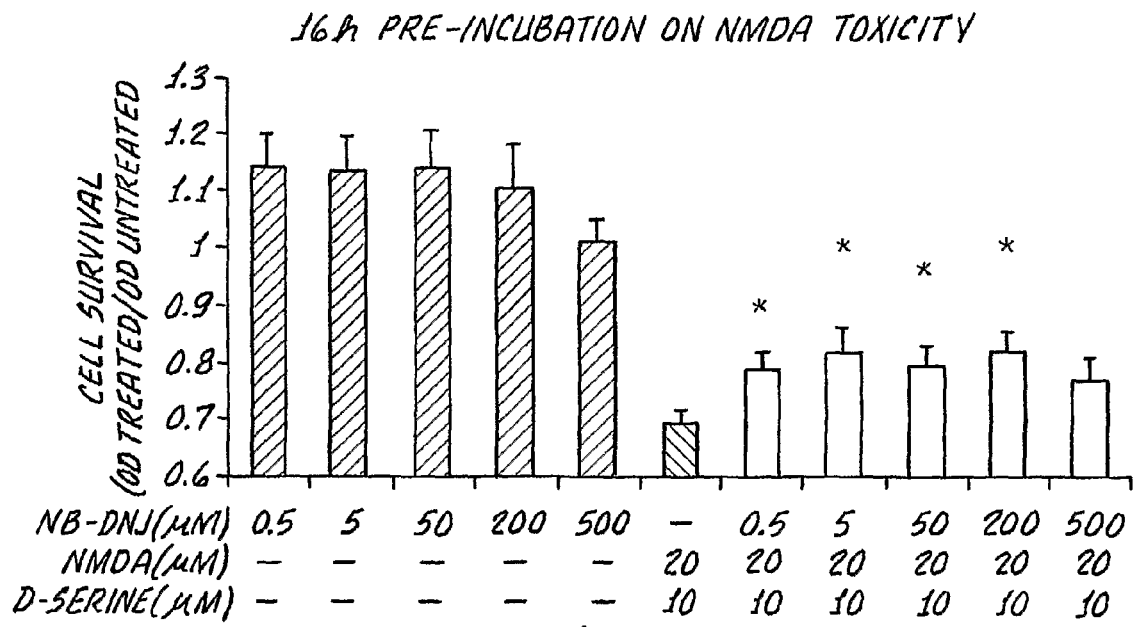
FIG. 8B shows the effect of 16 hours' preincubation with NB-DNJ on neural cells in culture subsequently treated with NMDA.

Administration of NB-DNJ reduced neuronal death in a dose-dependent manner after either NMDA/serine treatment (FIGS. 8A and 8B) or kainate-induced toxicity. In the latter example, NB-DNJ is active without any preincubation, although it is generally seen that the neuroprotective effect is enhanced with the length of pre-incubation time of NB-DNJ before addition of the toxic agent. An asterisk (*) indicates significant difference in the response of the cells from a treatment with the toxic agent alone at $P<0.05$, using Wilcoxon test.

Figure 9A:
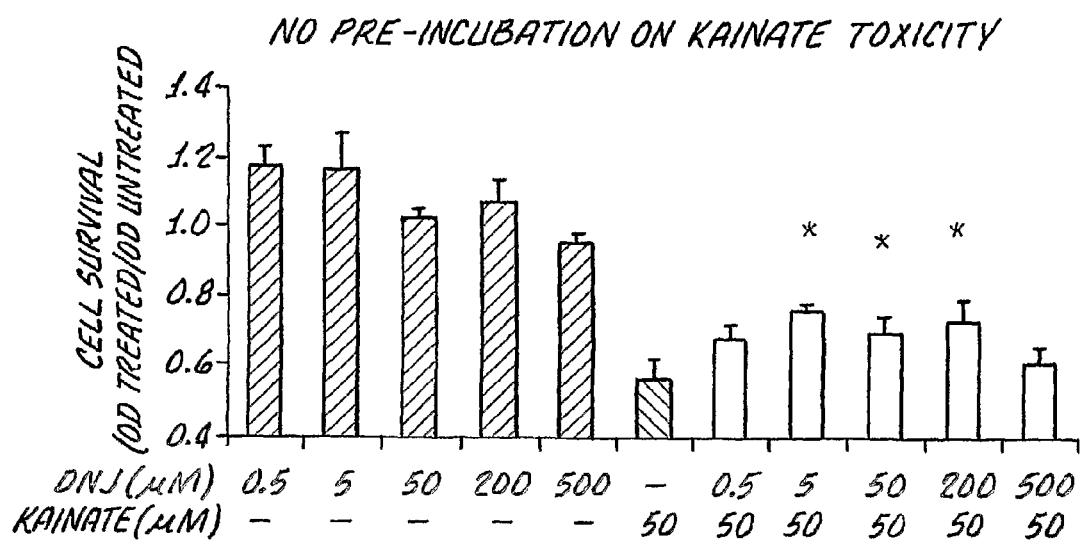
FIG. 9A shows the effect of various doses of DNJ on kainate-treated neural cells in culture.
Figure 9B:
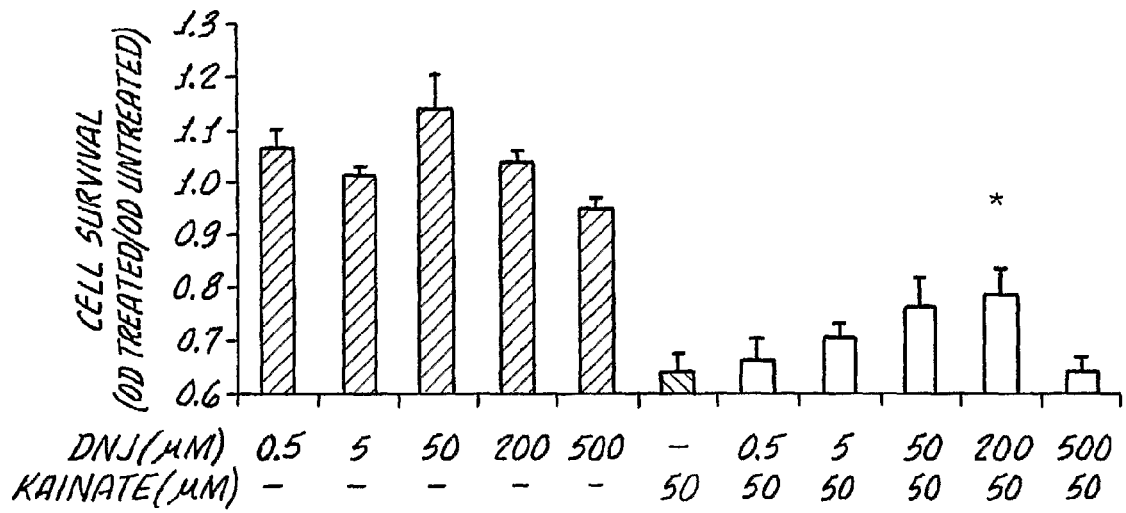
FIG. 9B shows the effect of 3 hours' preincubation with DNJ on neural cells in culture subsequently treated with kainate.
Figure 9C:
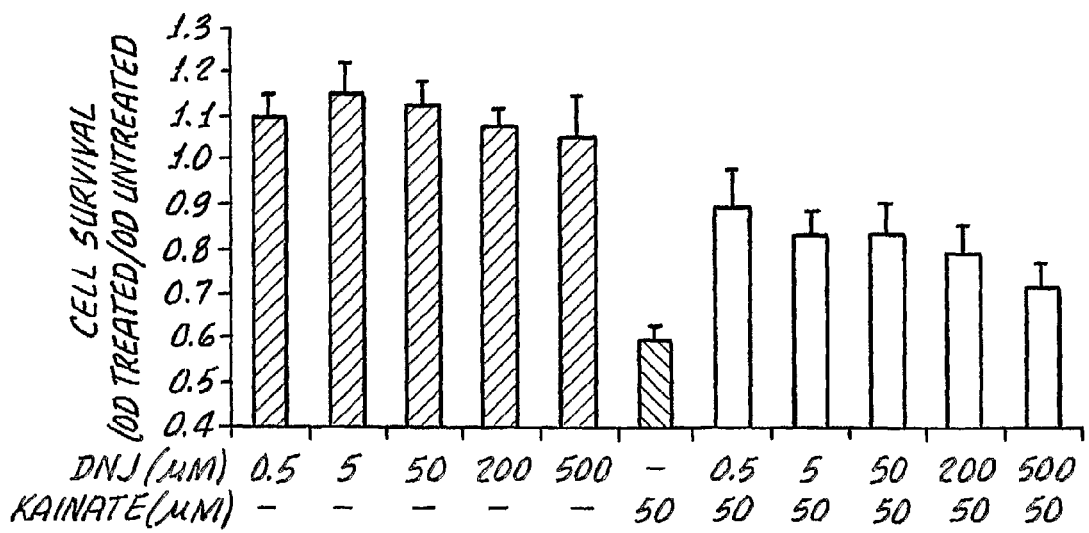
FIG. 9C shows the effect of 16 hours' preincubation with DNJ on neural cells in culture subsequently treated with kainate.

DNJ treatment of cortical cell cultures (FIGS. 9A, 9B and 9C) present a selective effect against kainate induced toxicity, for which DNJ affords about 50% protection.

Figure 10A:
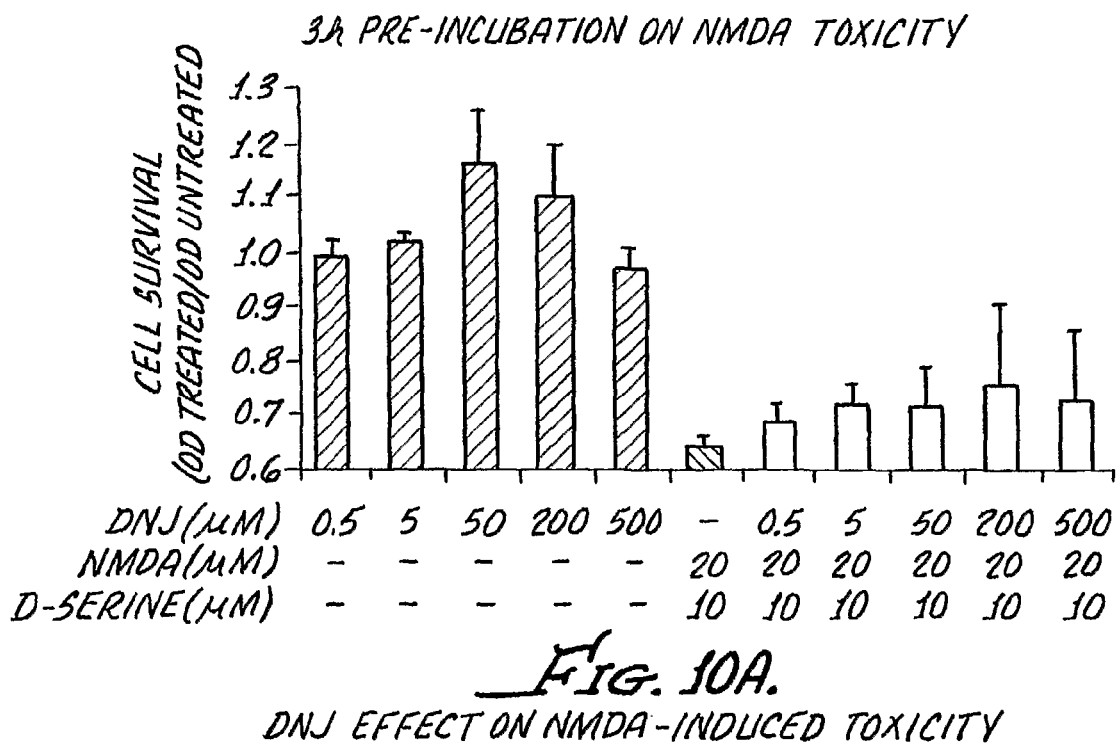
FIG. 10A shows the effect of 3 hours' preincubation with DNJ on neural cells in culture subsequently treated with NMDA.
Figure 10B:
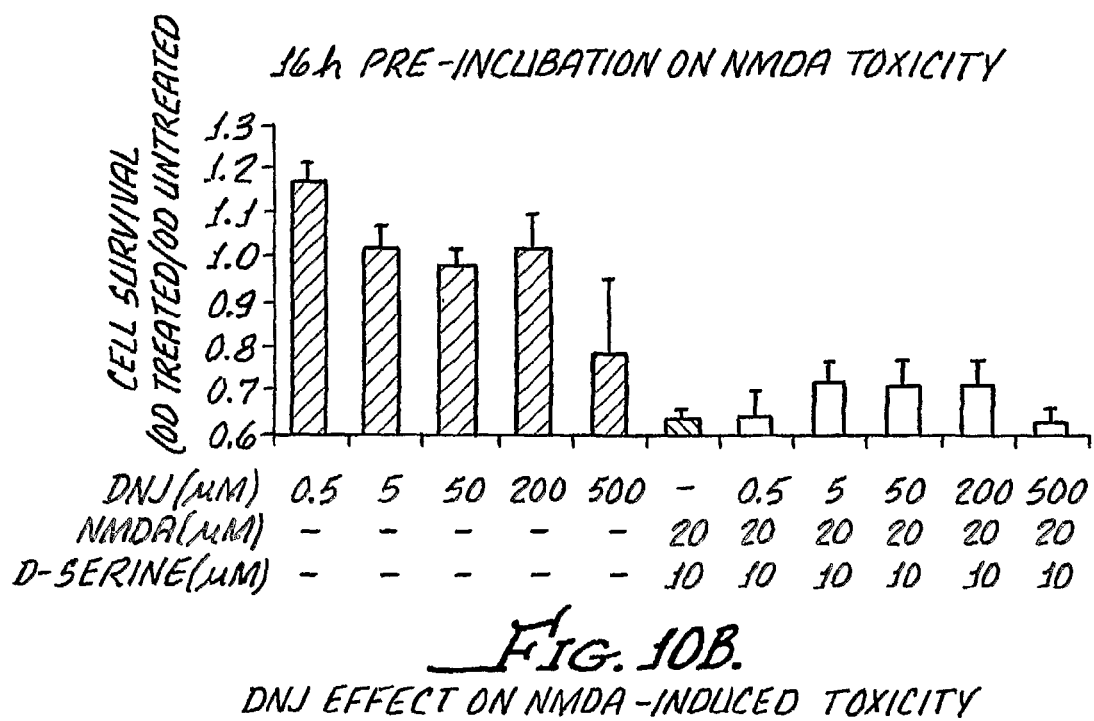
FIG. 10B shows the effect of 16 hours' preincubation with DNJ on neural cells in culture subsequently treated with NMDA.

In contrast, no neuroprotective effect is observed on NMDA/serine-treated cells treated with DNJ (FIGS. 10A and 10B), indicating that NB-DNJ selectively protects cortical cells from kainate-induced excitotoxicity, but not from NMDA/serine-induced toxicity. An asterisk (*) indicates that the differences in cell survival when comparing cells treated with the toxic agent versus those treated with kainate are statistically significant, at $P<0.05$, using Wilcoxon test.

NB-DNJ and molecules having structural similarity to NB-DNJ are thus able to preserve neuronal viability during periods of neural activation (stress) linked to excitotoxicity. Furthermore, NB-DNJ and molecules having structural similarity to NB-DNJ do not show any significant intrinsic cytotoxicity. Experimental evidence shows that such molecules exert a protective action without any preincubation. While not wishing to be limited by theory, Applicants believe that these compounds affect not only the cytotoxic events mediated by an overstimulation of receptors, but also the intracellular cytotoxic mechanisms following receptor activation, such as, without limitation, limiting calcium ions influx into the cell and consequent processes leading to cell death.

Other embodiments will be apparent to one of skill in the art in light of the present specification.

The following claims are drawn to these and additional embodiments of the invention.

What is claimed is:

1. A method for the treatment of chronic pain in a mammal in need thereof comprising administering to said mammal a composition containing an effective amount of a compound selected from the group consisting of NB-DNJ, D-glucaro-delta-lactam, and N-ethyl-1-deoxynojirimycin (NE-DNJ).

2. The method of claim 1 wherein said compound is NB-DNJ.

3. The method of claim 1 wherein said compound is D-glucaro-delta-lactam.

4. The method of claim 1 wherein said compound is NE-DNJ.

* * * * *

UNITED STATES PATENT AND TRADEMARK OFFICE
CERTIFICATE OF CORRECTION

| | | |
|---|---|---|
| PATENT NO. | : 7,884,115 B2 | Page 1 of 1 |
| APPLICATION NO. | : 11/575947 | |
| DATED | : February 8, 2011 | |
| INVENTOR(S) | : John E. Donello et al. | |

It is certified that error appears in the above-identified patent and that said Letters Patent is hereby corrected as shown below:

Title Page;

On the first page, in field (56), under "OTHER PUBLICATIONS" in column 2, line 10, delete "D-glucero-δ-lactam," and insert -- D-glucaro-δ-lactam, --, therefor.

On the first page, in field (56), under "OTHER PUBLICATIONS" in column 2, line 11, delete "Moeiji" and insert -- Meiji --, therefor.

In column 5, line 9, delete "laterial" and insert -- lateral --, therefor.

Signed and Sealed this
Fifth Day of April, 2011

David J. Kappos
*Director of the United States Patent and Trademark Office*